US006292695B1

(12) United States Patent
Webster, Jr. et al.

(10) Patent No.: US 6,292,695 B1
(45) Date of Patent: Sep. 18, 2001

(54) METHOD AND APPARATUS FOR TRANSVASCULAR TREATMENT OF TACHYCARDIA AND FIBRILLATION

(76) Inventors: Wilton W. Webster, Jr., 3333 Diamond Canyon Rd., Diamond Bar, CA (US) 91765; Benjamin J. Scherlag, 11403 Spring Hollow Rd., #207, Oklahoma City, OK (US) 73120; Michael Scherlag, 7304 NW 111th Ter., Oklahoma City, OK (US) 73162; Patrick Schauerte, 6490 N. Warren, #270 Chevy Chase Apts., Oklahoma City, OK (US) 73116

( * ) Notice: Subject to any disclaimer, the term of this patent is extended or adjusted under 35 U.S.C. 154(b) by 0 days.

(21) Appl. No.: 09/334,822

(22) Filed: Jun. 17, 1999

Related U.S. Application Data

(60) Provisional application No. 60/110,054, filed on Nov. 25, 1998, and provisional application No. 60/090,009, filed on Jun. 19, 1998.

(51) Int. Cl.[7] ................................................... A61N 1/368
(52) U.S. Cl. ................................ 607/14; 607/99; 607/113; 607/122; 607/148
(58) Field of Search ........................... 607/14, 9, 98, 607/99, 101, 113, 122, 126, 128, 148, 149, 154; 606/32, 41

(56) References Cited

U.S. PATENT DOCUMENTS

| 5,411,531 | 5/1995 | Hill et al. .............................. 607/14 |
| 5,466,245 | 11/1995 | Spinelli et al. ......................... 607/17 |
| 5,492,119 | 2/1996 | Abrams ................................. 128/642 |
| 5,700,282 | 12/1997 | Zabara .................................... 607/9 |
| 5,772,590 | 6/1998 | Webster, Jr. ......................... 600/374 |
| 5,876,336 | 3/1999 | Swanson et al. .................... 600/374 |

OTHER PUBLICATIONS

Cooper et al., Neural Effects on Sinus Rate and Atrioventricular Conduction Produced by Electrical Stimulation from a Transvenous Electrode Catheter in the Canine Right Pulmonary Artery, Circulation Research vol. 46, No. 1, Jan. 1980.

Chiou, C.W. et al., Efferent Vagal Innervation of the Canine Atria and Sinus and Atrioventricular Nodes. Circulation 1997;95:2573–2584.

Murphy, DA, et al., Preliminary Observations on the Effects of the Stimulation of Cardiac Nerves in Man. Can J Physiol Pharmacol 1985;63:649–655.

Schwartz et al., Prevention of Sudden Cardiac Death After a First Myocardial Infarction by Pharmacologic of Surgical Antiadrenergic Interventions, Publ. Nov. 1991, pp. 2–16.

Zipes, Douglas P., Arrtythmogenic Role of Autonomic Intervation during Ischemia/Infarction and the Long QT Syndrome, Journal of Cardiovascular Electrophysiology, vol. 2, No. 2, Supplement, April 1991, pp. S92–S98.

Quan et al. (PACE 19:647, 1996).

(List continued on next page.)

Primary Examiner—Kennedy Schaetzle
(74) Attorney, Agent, or Firm—Christie, Parker & Hale, LLP

(57) ABSTRACT

The present invention provides a method of controlling cardiac fibrillation, tachycardia, or cardiac arrhythmia by the use of an electrophysiology catheter having a tip section that contains at least one stimulating electrode, the electrode being stably placed at a selected intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

61 Claims, 11 Drawing Sheets

OTHER PUBLICATIONS

Lazzara, R., et al., Selective in Situ Parasympathetic Control of the Canine Sinoatrial and Atrioventricular Node. Circulation Research 1973; 32:393–401.

Chen, SA, et al., Intracardiac Stimulation of Human Parasympathetic Nerve Fibers Induces Negative Dromotropic Effects: Implication with the Lesions of Radiofrequency Catheter Ablation. Cardiovasc Electrophysiol 1998;9:245–252.

Leenhardt, A., et al., Catecholaminergic Polymorphic Ventricular Tachycardia in Children, American Heart Association, Circulation, vol. 91, No. 5, Mar. 1, 1995, pp 1512–1519.

Stevenson, W.G., Cardiac Sympathectomy to Prevent Sudden Death, J. Cardiovasc Electrophysiol. vol. 3, pp 17–20, Feb. 1992.

Armour, J.A., et al., Gross and Microscopic Anatomy of the Human Intrinsic Cardiac Nervous System, The Anatomical Record, 247:289–298 (1977).

Vanoli, E., et al., Vagal Stimulation and Prevention of Sudden Death in Conscious Dogs with a Healed Myocardial Infarction, Circulation Research, vol. 68, No. 5, May 1991, pp 1471–1481.

Tsai, C., et al., Bezold–Jarisch–Like Reflex During Radiofrequency Ablation of the Pulmonary Vein Tissues in Patients with Paroxysmal Focal Atrial Fibrillation, Journal of Cardiovascular Electrophysiology, vol. 10, No. 1, Jan. 1999, pp 27–35.

Scherlag, M.A., et al., Transvenous Parasympathetic Cardiac Nerve Stimulation: A new Approach For Sinus Rate Control, NASPE Abstracts, PACE, vol. 22, Apr. 1999, Part II, pp 699.

Schauerte P.N., et al., Atrial Fibrillation Initiated by Extopic Beats Originating in the Pulmonary Veins and the Superior Vena Cava: Reproducible Induction by Cardiac Autonomic Nerve Stimulation, NASPE Abstracts, PACE, vol. 22, Apr. 1999, Part II, pp 768.

Scherlag, B.J., et al., Radiofrequency Ablation at the Junction of the Superior Vena Cava and Right Atrium Terminates Neurally Induced Atrial Fibrillation, NASPE Abstract, PACE, vol. 22, Part II, pp 724.

Schauerte, P.N., Ventricular Rate Control During Atrial Fibrillation by Cardiac Parasympathetic Nerve Stimulation: A Transvenous Approach, NASPE Abstracts, PACE, vol. 22, Apr. 1999, Part II, pp 754.

Thompson, G. W., Bradycardia Induced by Intravascular Versus Direct Stimulation of the Vagus Direct, Ann Thorac Surg., 1998:65:637–42.

Shusterman, V., et al., Autonomic Nervous System Activity and the Spontaneous Initiation of Ventricular Tachycardia, JACC vol. 32, No. 7, Dec. 1998:1891–9.

Haissaguerre, M., Radiofrequency Catheter Ablation in Unusual Mechanisms of Atrial Fibrillation:Report of Three Cases, Journal of Cardiovascular Electrophysiology, vol. 5, No. 9, Sep. 1994.

A. SVC Stimulation during Pacing induced AF--60 Volts

B. SVC Stimulation during Pacing induced AF–90 Volts

A. Regular Pulsing-130 Volts (pulse CL=300 ms, duration=10 ms)

B. Irregular Pulsing-130 Volts (pulse duration=10 ms)

METHOD AND APPARATUS FOR TRANSVASCULAR TREATMENT OF TACHYCARDIA AND FIBRILLATION

CROSS-REFERENCE TO RELATED APPLICATIONS

This application claims the benefit of Provisional Application Nos. 60/110,054 filed Nov. 25, 1998, and 60/090,009 filed Jun. 19, 1998, both of which are herein incorporated by reference.

BACKGROUND OF THE INVENTION

The field of the invention is the control of tachycardia, including fibrillation, and arrhythmias, particularly the control of atrial fibrillation and ventricular tachycardia.

Tachycardia is the rapid beating of the heart, caused by abnormalities in any part of the heart, for example the atria, Purkinje system, or ventricles. Often, the extremely rapid beating of the heart is uncoordinated, and leads to fibrillation or flutter. These conditions occur after myocardial infarctions, for example, or in various pathological conditions, such as a dilated heart, blockage of the Purkinje system, or following chemical therapies (e.g., epinephrine) or repetitive stimulation. Atrial flutter often becomes atrial fibrillation within a few days or weeks, and leads to a complete failure of the atria to pump blood.

Atrial fibrillation is the most frequent tachycardia in patients. It most frequently occurs in patients over the age of 60 years, and affects over 8% of patients with cardiovascular disease and people older than 80 years (1, 2). Chronic atrial fibrillation doubles mortality (3), mostly due to an increased risk of stroke as well as other cardiovascular complications. Among other risk factors, congestive heart disease imposes the highest risk for developing atrial fibrillation (4.5–5.9 fold) (4). Therefore, restoration of normal sinus rhythm by pharmacological or electrical cardioversion is attempted in many patients with atrial fibrillation. Unfortunately, atrial fibrillation recurrence rates one year after successful cardioversion are high (75% without antiarrhythmic drug prophylaxis and 50% with aggressive antiarrhythmic medication; (5)). Moreover, the likelihood of cardioversion success is low in patients with chronic atrial fibrillation lasting longer than 2 years or who have enlarged atria (6). In many of these patients, therapy is directed toward ventricular rate control during atrial fibrillation in order to stabilize cardiac function. However, in patients with concomitant heart failure, drugs that slow the ventricular rate during atrial fibrillation may further depress ventricular contractility and cause arterial hypotension or be of limited use due to side effects.

Like atrial fibrillation, ventricular tachycardia can lead to fibrillation, which leads to failure of the ventricles to pump blood. Unlike atrial fibrillation, ventricular fibrillation cannot be compensated for by the rest of the heart and rapidly leads to sudden death if not reversed. Ventricular fibrillation is a common cause of death in patients (7). For example, patients who survive myocardial infarction often remain at risk for reentrant ventricular tachycardia. The sympathetic and parasympathetic nerves (autonomic innervation) of the heart influence susceptibility to spontaneous arrhythmias. Sympathetic stimulation can increase the risk of fatal arrhythmias during ischemic events and parasympathetic stimulation can decrease the risk (8). Current efforts to control this excess sympathetic tone include administration of β-adrenergic blocking drugs and surgical sympathectomy (9). Problems with these methods include contraindications for drug therapy in patients who are sensitive to the negative inotropic effects of β-adrenergic blockade and the inherent risks of thoracic surgery, which in this case also include pulmonary complications, injury to the brachial plexus, and upper extremity paresthesias.

Another common measure used to control atrial or ventricular tachycardia is ablation or modification of the His bundle or atrioventricular node and ablation of atrial or ventricular foci. Such ablation may abolish a tachycardia or slow the ventricular response during atrial fibrillation by blocking impulse conduction across the atrioventricular node. Ablation can be performed by introduction of a catheter into the heart through the venous system and subsequent ablation of the tissue.

In 1973, Lazzara and Scherlag reported that electrical stimulation of parasympathetic cardiac nerves at the junction of the right atrium and the inferior vena cava close to the coronary sinus ostium selectively prolonged atrioventricular (AV) conduction time (10). Chen et al. showed control of ventricular rate during atrial fibrillation by short bursts of stimulation to parasympathetic nerves in the fat pads to the AV node, but this method can lead to unwanted stimulation of myocardial muscle, and stimulation times are necessarily very brief because the electrode cannot be stably maintained in the appropriate location. Most recently, Reek et al. (12) reported that stimulation of the parasympathetic nerve fibers in the RPA with a conventional electrode catheter decreased the sinus rate in sheep. In addition, electrical stimulation of parasympathetic nerves either during coronary artery bypass grafting operation (CABG) (13) or after CABG operation (14) have demonstrated that parasympathetic fibers innervating the sinus and atrioventricular node can also be stimulated in humans. The stimulation electrodes, however, were only temporarily fixed at the outer surface of the heart or superior vena cava. Chiou et al. demonstrated that extracardiac electrical stimulation of parasympathetic fibers in fat pad between the superior vena cava, the aorta, and adjacent to the right pulmonary artery, diminished AV nodal conduction during sinus rhythm (15). These results required a thoracotomy. Most recently, Thompson and coworker reported that endovascular electrical stimulation of parasympathetic fibers in the superior vena cava with a conventional electrode catheter slows the sinus rate (16).

SUMMARY OF THE INVENTION

The present invention provides a method and system for controlling the heart rate of a patient and is particularly useful in controlling cardiac fibrillation and tachycardia. The method involves the intravascular stimulation and/or ablation of cardiac parasympathetic and sympathetic nerves sufficient to regulate or slow the heart rate or prevent the occurrence of these arrhythmias.

The method comprises providing an electrophysiology catheter comprising at least one electrode and preferably an electrode array, e.g., in an expandable electrode basket, at its distal end. The catheter is inserted into a blood vessel and directed to a location wherein the electrode through which a stimulus is delivered is adjacent to one or more predetermined cardiac parasympathetic or sympathetic nerves. A selected stimulus preferably a pulsed electrical signal, is then delivered through the electrode(s) to slow or regulate the beating rate of the heart. The stimulus is maintained for an extended period to provide a physician sufficient time to administer a drug, operate or take other appropriate measures to attempt to permanently or at least more permanently establish normal heart rhythm or slow the heart rate. Such a period may require several hours.

The selected stimulus is preferably below the threshold needed to depolarize the cardiac muscle or it is applied sufficiently far from the cardiac muscle so that depolarization does not occur. Alternatively, a stronger stimulus intensity may be used if it is timed to occur during the myocardial refractory period. The refractory period can be induced at regular intervals by pacing the contraction of the myocardium with electrical pulses applied from the same or a different electrode as is used to apply the nerve stimulation.

A preferred stimulus for stimulating a predetermined parasympathetic nerve is a pulsed electrical signal having a frequency of from about 1 to about 200 Hz, preferably about 20–30 Hz, having an intensity or strength of from about 1 to about 200 volts as measured at the electrode tissue interface, preferably from about 8 to about 15 volts. The duration of each stimulating pulse is from about 1 microsecond to about 10 milliseconds, preferably from about 50 $\mu$sec (0.05 ms) to about 600 Asec (0.6 ms), most preferably from about 50 $\mu$sec to about 100 $\mu$sec.

It is understood that the frequency, intensity and duration of the signal may vary. For example, depending on the precise location of the electrode through which a stimulus is delivered and the nerve to be stimulated, a signal of greater or lesser strength may be required. In such a situation, the stimulus can be varied during the procedure until the desired slowing of the heart rate is achieved. That is, if no response is achieved initially, the voltage may be increased in steps, e.g., of 5–10 volts/step until a response is seen. Likewise, the frequency, pulse duration and polarity may be adjusted. Clearly, other parameters may be varied including the location of the electrode to achieve and/or improve the response.

It is further understood that the stimulating signal may be of sufficient intensity, frequency and duration to ablate the nerve. This is done, for example, if a patient is at high risk of ventricular tachycardia from cardiac sympathetic stimulation, common after myocardial infarction, where the patent has vagally maintained atrial fibrillation (17). Stimulation frequencies in the radiofrequency range (e.g., over 10 kHz) can be used for ablation. Alternatively, ablation may be achieved by any other suitable means, for example any thermal means or cryoablation means.

Preferred intravascular sites for stimulation of parasympathetic nerves include the right pulmonary artery, the superior vena cava, and the coronary sinus. Stimulation at these sites is useful to control a variety of arrhythmias and tachycardias, including atrial fibrillation and ventricular tachycardia.

The system comprises a catheter, preferably a steerable catheter having a tip section containing one or more electrodes. The catheter may be any type that can be safely placed and maintained in a desired location in a blood vessel without unduly impeding blood flow. A preferred catheter for use in the invention has a variably expandable electrode section, most preferably a basket catheter having a basket assembly at the catheter's distal end. The basket assembly comprises a plurality of splines connected at their proximal and distal ends, at least one and preferably all splines comprising at least one electrode. The basket assembly is movable between a collapsed arrangement and an expanded, "bowed-out" arrangement. Preferably, the basket assembly, in its expanded arrangement, has a length of from about 2 cm to about 6 cm, preferably from about 2 to about 4 cm and a diameter of from about 10 to about 30 mm, preferably about 10 to about 20 mm. The splines of the basket catheter may carry one or more electrodes or may form electrodes themselves. In a preferred embodiment, each spline has an uninsulated central section which can serve as an electrode and one or more ring or wrapped electrodes on the insulated end portions of the spline. The basket arrangement allows very precise and stable localization of stimulation.

The system further comprises a low frequency pulsed signal generator electrically connected to the stimulating electrode for generating a stimulating signal, a monitor and/or display for recording and/or displaying the patient's heartbeat rate and one or more indifferent electrodes. In a particularly preferred embodiment of the invention, the system further comprises a programmable controller which is electrically connected to the pulse generator and to a sensor which senses the heartbeat rate of the patient. The controller, when activated, is programmed to stimulate each electrode of the electrode array to determine which is closest to the nerve and to vary, preferably in a stepwise fashion, one or more of the intensity, frequency or pulse duration of the stimulating signal to achieve the desired lowering of the heartbeat rate.

The present invention avoids the disadvantages of previous therapies. It provides a consistent and stable means for transvascular electrical stimulation and/or ablation (denervation) that affects cardiac parasympathetic and sympathetic nerves, effecting a decrease in the rapid atrial and ventricular responses during atrial fibrillation and other tachycardias without affecting ventricular contractility. The invention's transvenous approach to parasympathetic or sympathetic nerves offers an improved opportunity for acute and chronic ventricular rate control during atrial or ventricular tachycardia or fibrillation and other arrhythmias without concurrent stimulation of the heart muscle itself, and without the use of contraindicated drugs. Unlike previous intravascular stimulation efforts, the expandable or basket catheter of the invention allows long term, stable placement of the electrode for accurate, repeatable stimulation at the desired location. Additionally, the short pulse duration reduces the risk of unwanted myocardial stimulation.

DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The present invention provides a system comprising a minimally invasive catheter and low frequency pulsed signal generator for treating and preventing atrial and ventricular tachycardia and cardiac arrhythmias by specific stimulation of parasympathetic or sympathetic nerves innervating the heart. The invention also provides a system comprising a minimally invasive catheter and an ablation signal generator for treating and preventing tachycardia by specific ablation of parasympathetic and/or sympathetic nerves innervating the heart. As used herein, "tachycardia" means the rapid beating of the heart, and can include fibrillation and flutter. "Fibrillation" means an uncoordinated contraction of cardiac muscle, leading to inefficient pumping of the heart. "Flutter" means an extremely rapid beating.

Figure 1:
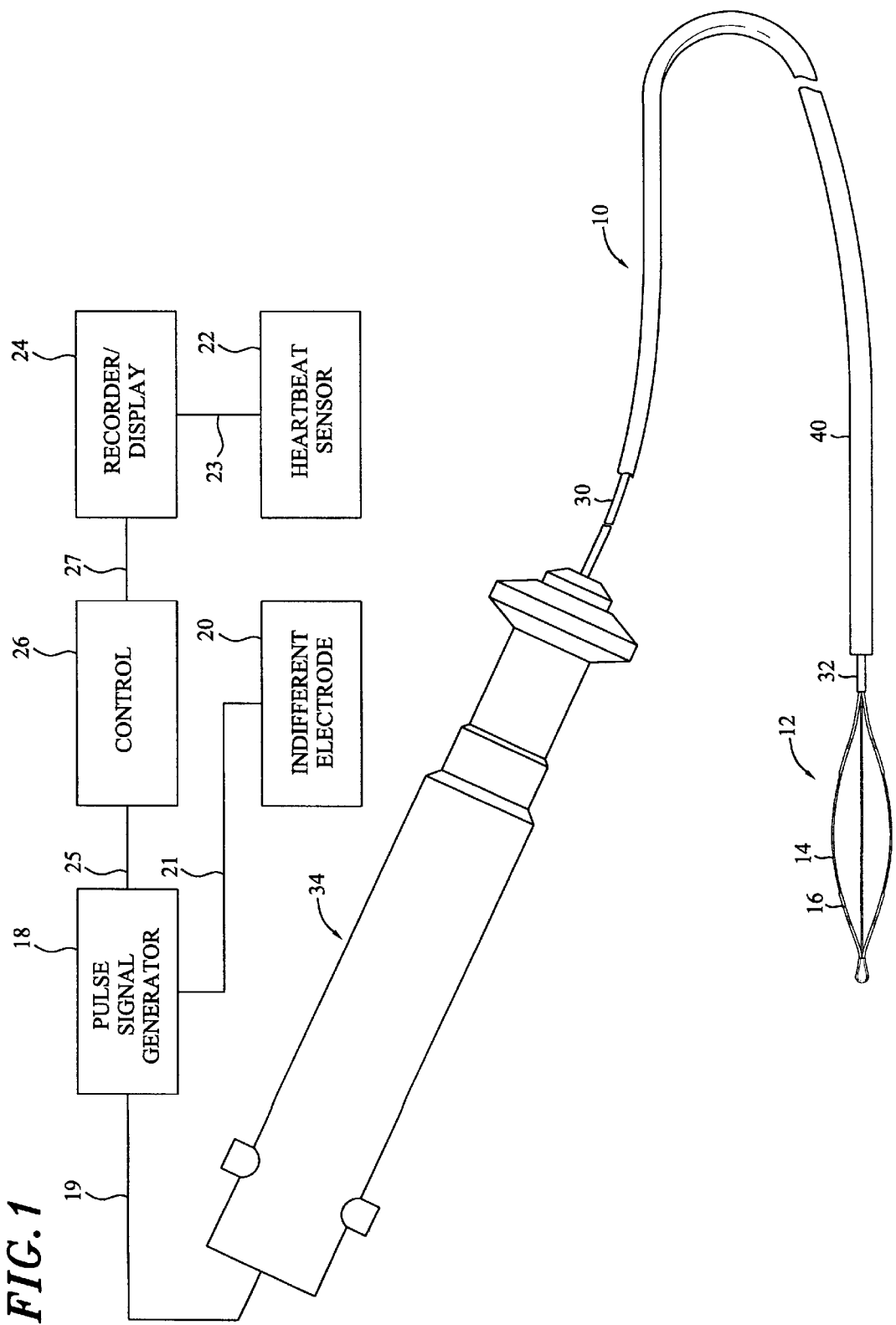
FIG. 1: A schematic of a preferred system for regulating the heart rate of a patient.
Figure 2A:
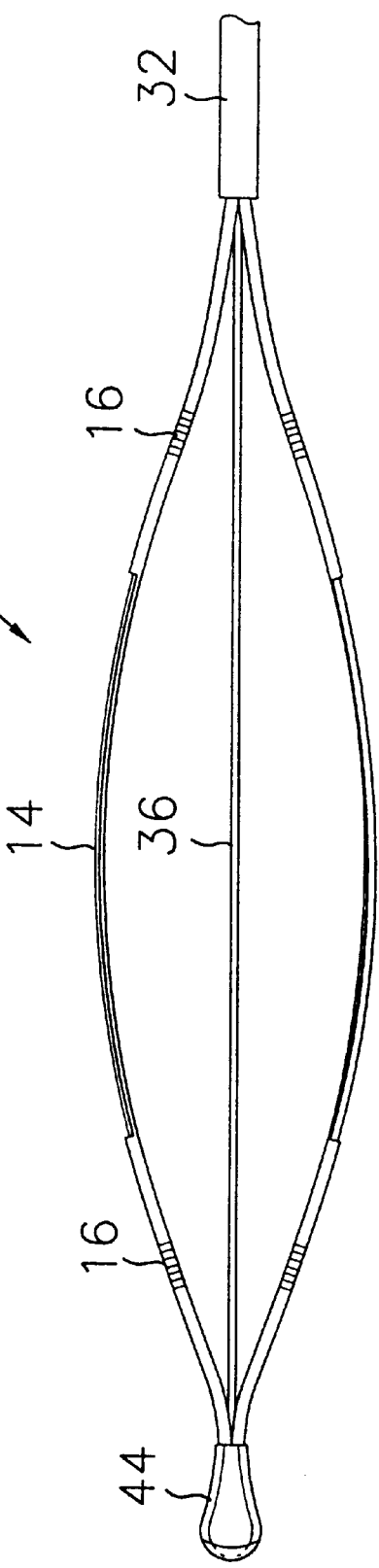
FIG. 2A: Enlarged view of the distal end of the catheter of the system shown in FIG. 1.
Figure 2B:
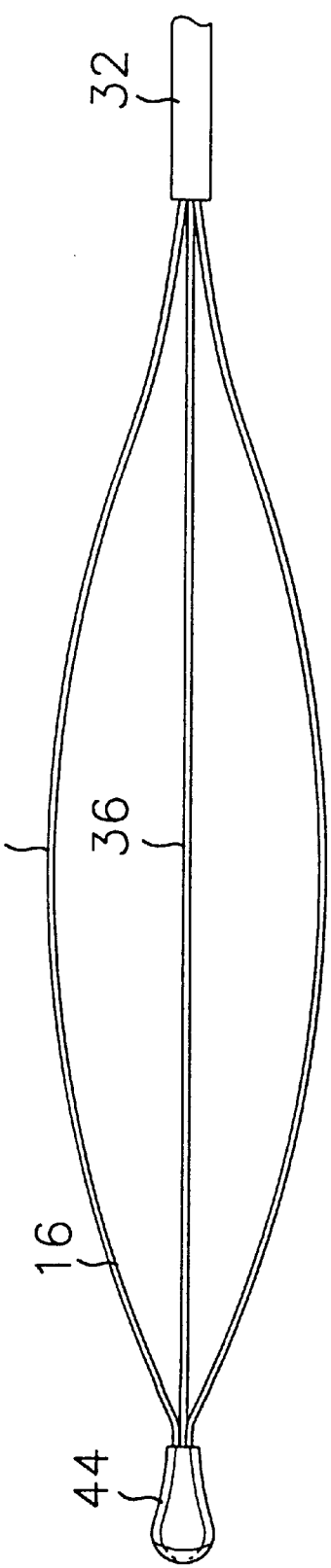
FIG. 2B: Enlarged view of the distal end of a preferred catheter used for ablation, having splines uninsulated along their entire length.

A preferred system in accordance with the present invention is shown in FIGS. 1 and 2. The system comprises a steerable catheter 10, having an expandable basket assembly 12 at its distal end. The basket assembly 12 carries a plurality of electrodes 14 and 16 which are electrically connected to a signal generator 18 by electrode lead wires (not shown) which extend through the interior of the catheter and electrical connection 19. One or more indifferent electrodes 20 which are placed on the patient's skin are also electrically connected to the signal generator 18 by electrical connection 21.

The signal generator 18 is capable of generating a signal having a frequency from about 1 to about 20 Hz, preferably about 20 to about 30 Hz and having an intensity of from about 1 to about 150 volts, preferably from about 8 to about 15 volts and a pulse duration of from about 1 microsecond to about 10 milliseconds, preferably from about 50 to about 600 microseconds.

One or more sensors 22 are provided for monitoring the heartbeat of the patient. The sensors are electrically connected via line 23 to a recorder/display 24 for recording and/or displaying the patient's heartbeat, preferably in the form of a conventional electrocardiogram or the like. In the embodiment shown, a programmable controller 26 is electrically connected to the signal generator 18 via line 25 and to sensors 22, e.g., via line 27 to recorder/display 24.

The catheter 10 comprises an elongated tubular catheter body 30, a tip section 32 at the distal end of the catheter body 30 and a control handle 34 at the proximal end of the catheter body 30. The catheter body 30 comprises an elongated tubular construction having a single, central or axial lumen. The catheter body 30 is flexible, i.e., bendable, but substantially non-compressible along its length. The catheter body 30 preferably comprises a tubular wall of high-strength braided stainless steel or other high-strength wire or fiber, sandwiched between inner and outer layers of firm, yet flexible, polyurethane. This high torque shaft structure allows a physician to control the orientation of the electrode basket by rotating the catheter body 30 where it enters the patient's body, which is usually at the groin or neck. The catheter body 30 preferably further comprises a nylon stiffening sleeve lining the interior of the tubular wall. A suitable construction of the catheter body is disclosed in U.S. Pat. No. 5,827,278 which is incorporated herein by reference. The outer diameter of the catheter body 30 is not critical but is preferably no more than about 8 French and more preferably no more than about 7 French. Likewise, the thickness of the outer wall is not critical.

The catheter tip section 32 comprises a short section of flexible tubing preferably having a diameter of about 6–7 French, and having a pair of off axis lumens. At the distal end of the tubing of the tip section, there is provided an expandable basket assembly 36. A preferred basket assembly construction is disclosed in U.S. Pat. No. 5,772,590, which is incorporated herein by reference. In such a construction, the basket assembly has five arms and a central puller wire. The arms are fixed at their proximal ends to a proximal fitting and also fixed at their distal ends to a distal fitting. The proximal fitting which has a central opening, is received by and fixed by glue or the like in a recess in the distal end of the tubing of the catheter tip section. The arms comprise a backbone made of metal, e.g., Nitinol, of semicircular cross section. The metal backbones are completely or partially covered with an insulation coating. One or more electrodes may be carried on the arms. In a preferred embodiment suitable for ablation, the entire surface of the spline is uninsulated.

A particularly preferred basket assembly 12 is shown in FIG. 2. In this embodiment, the outer surface of the middle half of the metal backbone of the arms (only two arms of five are shown) are exposed to form electrodes 14. Additionally, each arm contains a ring-type electrode 16 on the insulated portions of the arm both distally and proximally to the exposed backbone portion. Preferred ring-type electrodes are formed by wrapping a lead wire around the insulated coating a number of times and stripping the lead wire of its own insulated coating on its outwardly facing surfaces. Such electrodes are disclosed for example in U.S. Pat. No. 5,772, 590.

The particular construction of FIG. 2 involving an electrode configuration of partially exposed arms and adjacent wrapped electrodes is presently preferred because it has been found to increase current density in a small area, allowing up to a 50% decrease in the current needed to stimulate the nerve. This reduces the risk of tissue damage and other adverse effects. In its expanded arrangement, the basket assembly is preferably no more than about 6 cm long and preferably from about 2 to about 4 cm long. Also in its expanded arrangement, the diameter is adjustable to from about 10 to about 30 mm.

The catheter comprises a steering mechanism, for example, as described in U.S. Pat. No. RE 34,502 and U.S. patent application Ser. Nos. 09/157,055 (filed Sep. 18, 1998), 09/130,359 (filed Aug. 7, 1998), and 08/924,611 (filed Sep. 5, 1997), which are incorporated herein by reference. The steering mechanism comprises a puller wire (not shown) which extends from a proximal end in the handle through the catheter body and into an off axis lumen in the catheter tip section. Within the catheter body, the puller wire extends through a closely wound coil that is bendable but substantially compressible. The coil is fixed near the proximal and distal ends of the catheter body and prevents deflection of the catheter body.

The distal end of the puller wire is anchored in the tip section adjacent the proximal end of the basket. The proximal end of the puller wire is anchored to a movable member in the handle which can be moved relative to the catheter body. Proximal movement of the movable member relative to the catheter body. Proximal movement of the movable member relative to the catheter body results in deflection of the catheter tip section.

A second puller wire 36 extends through the catheter body, catheter tip section and is fixed to the distal fitting 44 of the basket. The second puller wire extends out of the proximal end of the catheter and into the handle for applying a proximally directed force to the puller wire. When the puller wire is moved proximally relative to the catheter body, the basket expands outwardly. Outward expansion of the basket forces the arms against the vessel walls, thereby impeding the motion of the arms relative to each other and resisting shifting of the basket within the vessel. Such a second puller wire arrangement is disclosed, for example, in U.S. Pat. No. 5,772,590.

The handle 34 may be of any suitable construction for manipulating a pair of puller wires. Preferably the handle has a pair of movable members to which the puller wires attach. Manual movement of the movable members results in longitudinal movement of the puller wires relative to the catheter body. Manipulation of one puller wire provides deflection of the tip section. Manipulation of the second puller wire provides expansion or elongation of the basket. Preferred handles and steering mechanisms for the catheter are described in U.S. patent application Ser. No. 09/130,359 (filed Aug. 7, 1998), and U.S. Provisional Patent Application No. 60/133,709 (filed May 12, 1999), which are also incorporated herein by reference.

It is understood that any suitable steering mechanism may be used. Alternatively, it is understood that the invention may be practiced without any steering mechanigm and/or without the use of a puller wire mechanism for expanding or elongating the basket. As to the latter, the basket may be expanded and contracted, for example, by moving the guarding sheath proximally off of the basket or distally over the basket.

It is understood that any suitable catheter that can suitably maintain a stimulating electrode at an intravascular location adjacent a parasympathetic or sympathetic nerve can be used. Stable placement means that the electrode remains relatively immobile for the time period of stimulation, so that one or repeated stimuli are applied to the same area, and the nerve fibers receiving the stimuli receive approximately the same stimulus intensity from identical stimulation pulses. If such a catheter comprises a basket assembly, any suitable basket assembly may be used. That is, the number and type, e.g., semi-circular cross section, of arms may vary as desired. Likewise, the number and type of electrodes on the arms may vary. If desired, the metal backbones of the arms may be completely exposed or completely covered. The tip section may comprise a single lumen rather than the two described above or, in the alternative, may comprise three or more lumens. Likewise, the catheter body may comprise more than one lumen if desired.

If desired, a non-basket catheter may be used. If so, it is preferred that the catheter comprise some mechanism for anchoring the stimulating against the wall of the blood vessel it is in. Such mechanisms include extendable corkscrew anchors. Examples of suitable anchoring mechanisms are disclosed in U.S. Pat. No. 5,431,168, which is incorporated herein by reference.

While it is presently preferred to use a guiding sheath, if the catheter comprises a mechanism for expanding and contracting the basket independent of the guiding sheath, a guiding sheath may not be required. This is particularly true if the catheter is steerable.

The catheter 10 is disposed within an outer guiding sheath 40 for placement at the desired intravascular location. The guiding sheath 40 covers the arms of the basket assembly internally in a collapsed position so that the entire assembly, consisting of the catheter 10 and guiding sheath 40, can be passed down a vein or artery to a desired location. To reach the desired intravascular location, the catheter and guiding sheath are inserted into a blood vessel and then guided to the desired site. During this procedure, the tip may be deflected as needed by manipulation of the first puller wire. Once the distal ends of the catheter 10 and guiding sheath 40 reach the desired location, the guiding sheath 40 is withdrawn. The second puller wire is then manipulated so that the arms of the basket assembly flex outwardly into their expanded arrangement. In such an arrangement the arms and the electrodes contact the walls of the blood vessel in which they are located.

Once the catheter basket is at the desired location, the controller 26 activates the signal generator 18 to transmit signals sequentially to each of the electrodes on the basket and to determine, based on signals received from the sensors 22 (indicating a response by the heart to the transmitted signals) which of the electrodes is closest to the nerve. If there is no response by the heart, the controller activates the signal generator to transmit a second signal sequentially to each of the electrodes, said second signal being different from the first signal in intensity, frequency or duration, preferably intensity. The controller continues this process until a response by the heart is received and the electrode(s) closest to the nerve in question is identified. If after a select period of time, if no response from the heart is sensed, the controller provides a signal, e.g., audible or visual, to the physician indicating that the electrode(s) are not sufficiently close to the desired nerve and that the catheter needs to be repositioned.

Once the electrode(s) nearest the desired nerve has been identified, the controller activates the pulse generator to transmit a stimulating signal to the identified electrode. If the response by the heart is insufficient, e.g., not enough slowing, the controller activates the pulse generator to vary the stimulating signal in one or more of the intensity, frequency and pulse duration, preferably in a stepwise fashion, until the desired slowing of the heartbeat rate is achieved. For example, a signal having an intensity sufficient to elicit a response from the heart may slow the heartbeat rate to some degree but not as much as is desired. Accordingly, the signal may be increased stepwise in intensity until the desired amount of slowing is achieved.

The parasympathetic nervous system produces its cardiac action primarily via vagal nerve fibers leading to cardiac ganglia. Sympathetic nerve fibers emerge from multiple cervical and paravertebral ganglia to provide a network of postganglionic nerve endings to the atria, ventricles, sinus node, and atrioventricular node. The terms "nerve" and "nerve fiber" as used herein includes a single neuron, a nerve, nerve ending(s), or nerve bundle, and if it is described as "autonomic," may be comprised of all parasympathetic, all sympathetic, or mixed parasympathetic and sympathetic fibers.

Because of the pattern of cardiac autonomic innervation, the invention can be practiced at numerous sites within the vasculature. In fact, any intravascular site which is adjacent to an autonomic fiber that innervates the heart is a potential site for the stimulation method of the invention. As used herein, "intravascular" means within the venous or arterial circulatory system, including blood vessels of all descriptions and chambers of the heart. When referring to "intravascular stimulation" in describing the method of the invention, it is meant stimulation from within the circulatory system resulting in (transvascular) stimulation of a tissue of interest. "Transvenous" or "transvascular" means across a blood vessel or across the wall of a cardiac chamber (including the connective, adipose, muscle, neural, and other associated tissue). "Stimulation" means a stimulus, usually electrical, which causes depolarization of a cell or cells, or portion of a cell, contraction, excitation as measured by e.g., calcium or sodium influx into the cell, or an altered membrane potential across a cell.

Appropriate sites for stimulation are those adjacent to cardiac autonomic nerves. Preferably the sites are sufficiently far from myocardial muscle that the muscle is not at risk of contraction during stimulation.

However, for some preferred sites, e.g., the coronary sinus, myocardial muscle is adjacent and can be stimulated by the autonomic stimulation. This is rarely a problem when the atria are in fibrillation, because the stimulation is incapable of causing coordinated atrial contraction.

Potential stimulation sites can be initially selected by reference to general anatomy; blood vessels of sufficient diameter for catheter access which are known to have autonomic fibers innervating the heart running nearby or adjacent are suitable candidates. Care must be taken, of course, to select locations with nerves that primarily innervate the area of interest so that other innervated areas are not affected. For example, three preferred intravascular parasympathetic sites at which a substantial reduction in ventricular rate during atrial fibrillation can be obtained are the ostium of the coronary sinus, the right pulmonary artery and the superior vena cava. Sympathetic bundles may be stimulated from discrete sites, for example, transvascularly from the aorta or the main pulmonary artery to the sympathetic fibers that run alongside. As will be apparent to one of skill in the art, the invention is not limited to sites directly adjacent to the heart, but can be practiced at any of the variety of sites (primarily thoracic) where blood vessels suitable for catheter access run parallel to or otherwise intersect with autonomic fibers serving the heart. Target fibers can thus be accessed from different sites on the patient, for example from near the subclavian, jugular, or azygous veins.

In accordance with the method of the invention, the catheter is introduced into a blood vessel and is guided by suitable means to a desired location. For example, fluoroscopic imaging can be used to guide the catheter to the selected site. In addition or alternatively, if the desired site is close to or within the myocardium, an electrode of the catheter may be used to sense electrical activity of the heart, such that when signals generated by the contraction of the cardiac muscle are detected, the sensing electrode is in the atrium. The catheter may then be advanced through the heart or withdrawn to reach the desired site. If the target site is just outside the heart, the catheter may be advanced or withdrawn until no myocardial contraction is detected. For example, if the target is the right pulmonary artery, the catheter would be advanced through the atrium, the tricuspid valve, and the right ventricle before exiting the heart and entering the right pulmonary artery. When contraction of the heart is no longer sensed, the catheter would be in a suitable position to begin testing for the desired stimulation location. Likewise, if the target is the superior vena cava, for example, sensing is performed from the catheter until atrial impulses are detected, indicating that the catheter is in the atrium. From that point, the catheter is slowly withdrawn until atrial signals are no longer detected. This would indicate that the catheter is in the superior vena cava.

Once a site is selected and the catheter is guided to the vicinity, accurate placement is made by slowly advancing or withdrawing the catheter, expanding it to hold it in place, and testing each electrode to identify the one closest to the selected nerve. If none of the arms are suitably close to the nerve, the expanded basket is contracted and moved slightly to another location. It is re-expanded and the electrodes re-tested. This process is repeated until adequate nerve stimulation is achieved.

Stimulation can be optimized by varying the intensity, frequency, polarity, and/or pulse duration of the signal. Of particular usefulness is changing the signal strength. A graded response of the ventricular rate during atrial fibrillation ranging from slight slowing to complete AV block can be accomplished. The desired level will be somewhere in between these extremes, and will vary depending on the patient's condition. Parameters and protocols for nerve stimulation can be any that produce the desired sympathetic or parasympathetic effects on the heart, and can be adjusted as needed for different patients or during an individual patient's treatment.

Figure 3:
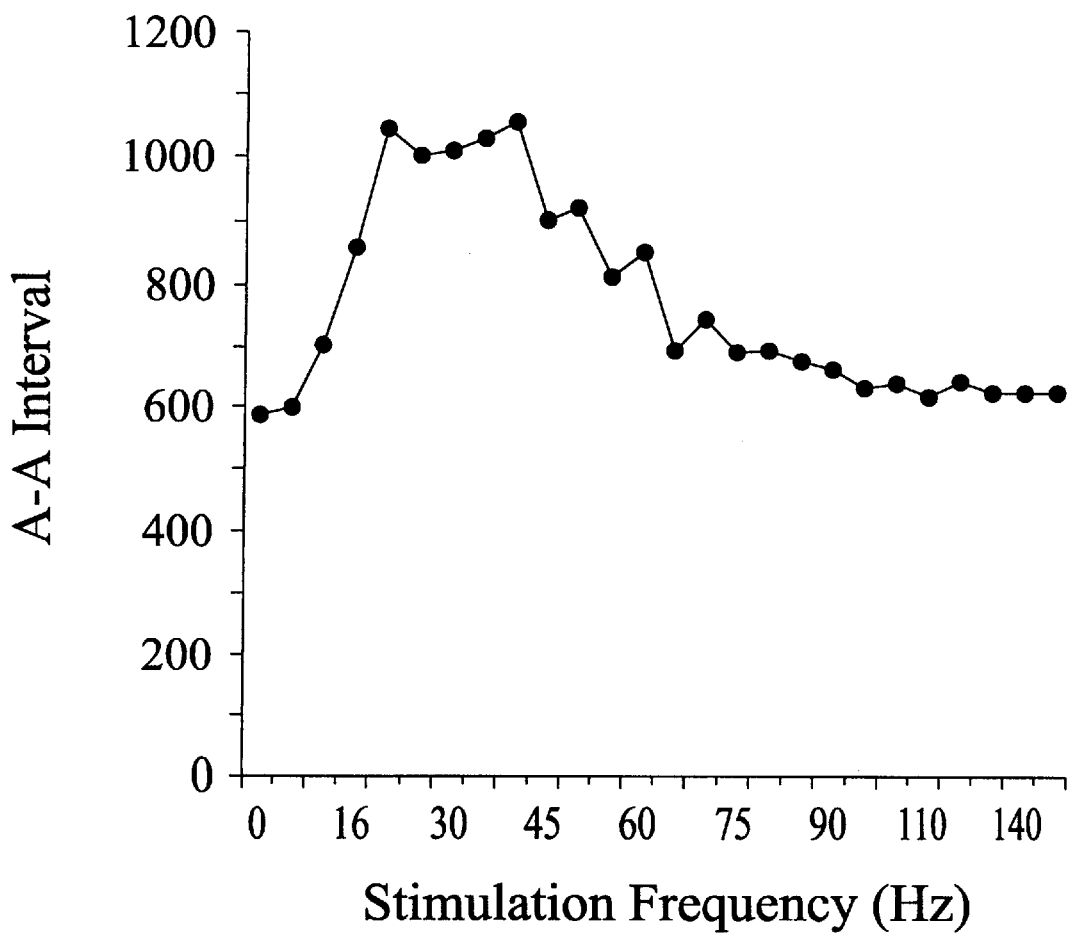
FIG. 3: Illustration of the influence of the frequency of cardiac nerve stimuli on the supraventricular rate slowing effect. In this dog, nerve stimulation was applied in the superior vena cava with an impulse duration of 0.1 ms and an intensity of 26 V. At a frequency of 20 Hz, the effect reached a plateau until it decreased at a frequency of 45 Hz.

In general, stimulus pulse duration, amplitude, polarity, and/or intensity can be modified. The pulse duration can be between about 1 microsecond to about 10 milliseconds, preferably about 100 $\mu$sec (0.1 ms); the frequency will be from about 1 to about 200 Hz, preferably from about 20–45 Hz; and the stimulus intensity will be from about 1 to about 150 V, preferably from about 8 to about 15 V. The range of stimulation frequencies possible, including the optimum range in the preparations tested is shown in FIG. 3. Frequencies between about 20 and 45 Hz showed the most preferable supraventricular rate slowing. The optimum signal will depend on the current density achieved at the stimulation site, the voltage drop across the stimulating equipment to the delivery site, and other factors well known to those of skill in the art. Lower voltages and frequencies are generally preferred, since they reduce the risk of tissue damage or any possible discomfort in patients arising from the stimulation. Shorter duration pulses are generally preferred because they reduce the possibility of depolarizing nearby muscle fibers.

If the selected stimulation site is adjacent to cardiac muscle, contraction of the muscle in response to the nerve stimulation can be avoided by timing the stimuli to coincide with the myocardial refractory period (when no amount of stimulation will induce contraction of the muscle). If this is done, a stronger signal may be used. If desired, concurrent pacing of the atria or ventricles can be performed to time the nerve stimulation to the heartbeat or refractory period of the muscle. Concurrent pacing can be performed with the same or a different catheter or electrode(s), and can be within the heart or vasculature or externally using any known methods. Likewise, recording or monitoring can be accomplished with the same or different electrodes or catheters.

The system and methods of the invention can be used to ablate sympathetic and parasympathetic nerves if necessary. Sympathectomy is indicated in certain patients, for example those with contraindications to $\beta$-blockers. Selective sympathetic denervation, performed by transvascular ablation using the method of the invention, can reduce these patients' risk of sudden death from acute arrhythmias. Selective parasympathetic denervation may be indicated in patients with atrial tachycardia or fibrillation induced or maintained by excessive vagal nerve stimulation. A denaturing or ablating stimulus (e.g., radiofrequency or cryoablation) is applied across the vessel wall to the sympathetic fibers at any desired location. Preferably, sites are selected where a purely or nearly pure sympathetic or parasympathetic branch runs very close to the vessel, and where there are few other nerves or other sensitive tissues. Ablating stimulation is applied until conduction in the fiber is impaired or ceases altogether. This can be monitored by any means, including recording from the heart to observe a change in heart rate. Such ablation is irreversible, and can be very selectively performed by first stimulating the nerve to determine its innervation sites and selecting an ablation location that maximizes the desired effect while minimizing unwanted ablation.

EXAMPLE 1

Surgical Preparation and Parasympathetic Cardiac Nerve Stimulation and Measurement Methods All animal studies were carried out in accordance with the guidelines for animal care and experimentation established by national agencies and were approved by the Research and Development Committee of the Department of Veterans Affairs Medical Center, Oklahoma City, Okla. In 33 adult mongrel dogs (weight 18–30 kg) anesthesia was induced with intravenous sodium pentobarbital (30 mg/kg body weight). During the experiment, 50 to 100 mg were injected as needed to maintain a sufficient depth of anesthesia. The dogs were intubated with a cuffed endotracheal tube and ventilated with room air using a positive pressure respirator (Harvard Apparatus Co., Natick, Mass., USA). A cannula was inserted into the left external jugular vein for fluid and drug delivery. Arterial blood pressure was monitored through a cannula in the right femoral artery. A quadripolar catheter with 2 mm interelectrode spacing was introduced into the left common carotid artery and advanced to the aortic root to record His bundle activity as described elsewhere (14, herein incorporated by reference). A right lateral thoracotomy was performed at the fourth intercostal space. After pericardiotomy the right atrium and the right ventricle were exposed. Pairs of plunge wire electrodes were inserted into the right atrial appendage and right ventricular apex for atrial and ventricular pacing, respectively, and local electrogram recording. Surface ECG lead II and aVR were monitored continuously. All tracings were amplified and digitally recorded using a computer-based Bard Labsystem (CR Bard Inc., Billerica, Mass., USA). ECG filter settings were 0.01 to 250 Hz, whereas bipolar electrograms were filtered at 30 to 250 Hz.

A custom designed 7 French basket catheter, a preferred embodiment of the catheter of the invention, was used for autonomic nerve stimulation (Cordis Webster Corp., Calif.). The catheter used in the present study used each arm as the electrode ("multiple-spline catheter;" portions of the arms were uninsulated). Bipolar electrical stimulation was done between adjacent arms of the basket. Periods of electrical stimulation lasting 10 seconds were delivered by means of a Grass stimulator (Astro-Med, Inc./Grass Instruments Division, West Warwick, R.I.) at a stimulation frequency of 20 Hz and a pulse duration of 0.05–0.1 ms. This level of stimulation has previously been demonstrated to be suitable for epicardial parasympathetic nerve fiber stimulation (10, herein incorporated by reference). Cardiac nerve stimulation at each of three stimulation sites, i.e., the coronary sinus, the right pulmonary artery, and the superior vena cava, was performed during atrial fibrillation. Atrial fibrillation was induced and maintained by constant rapid pacing at a cycle length of 100 ms from the electrodes in the right atrial appendage.

Group 1: Stimulation in the Coronary Sinus (n=10)

For parasympathetic stimulation in the coronary sinus, the catheter was introduced through the right or left external jugular vein. It was then advanced into the right atrium under fluoroscopic guidance. Positioning into the os of the coronary sinus was performed as described previously (13, incorporated by reference). When the coronary sinus had been entered, the basket was expanded to hold the catheter in a stable position against the endovascular surface. Stimulation over each adjacent pair of electrode arms was then attempted while the stimulus strength (SST) was increased stepwise from 7 to 50 V. If no visible slowing of the ventricular rate during atrial fibrillation was observed, the basket was contracted and the catheter gently rotated or advanced further into the coronary sinus until an effective stimulation site was found.

Group 2: Stimulation in the Right Pulmonary Artery (n=6)

For placement of the catheter in the right pulmonary artery the basket catheter was introduced through a purse string suture in the right ventricular outflow tract. It was then advanced under fluoroscopic control into the right pulmonary artery. Under fluoroscopy, the basket was positioned between the aorta and the atrial channel between the superior vena cava and inferior vena cava; however, electrode placement need not be done under fluoroscopic conditions. The sinus rate slowing was then assessed by stimulation over each adjacent pair of electrode arms at 40 V. If no visible ventricular rate slowing during atrial fibrillation occurred, the basket was contracted and withdrawn stepwise. Stimulation was repeated until a noticeable drop in ventricular rate during atrial fibrillation was achieved.

Group 3: Stimulation in the Superior Vena Cava (n=6)

For stimulation in the superior vena cava, the catheter was introduced through the right or left external jugular vein until a right atrial electrogram was recorded. The catheter was then withdrawn to a site at which no atrial signal was recorded. At this point the basket was expanded and the ventricular rate slowing effect during induced atrial fibrillation was assessed by stimulation over each adjacent electrode pair at 40 V. If no slowing effect was observed, the catheter was withdrawn and stimulation was repeated until a slowing response was obtained. A successful intravascular stimulation site was located in the proximal right pulmonary artery.

Once an effective coronary sinus, right pulmonary artery or superior vena cava site was identified, neural stimulation was started at 2 V and thereafter stepwise increased to a maximal voltage of 40 V. R—R intervals during cardiac nerve stimulation were measured in surface ECG leads II and aVR. At each stimulus intensity, 10 consecutive R—R intervals after the onset of cardiac nerve stimulation were measured for calculation of the mean R—R interval.

Measurement of Sinus Rate Slowing and Effective Refractory Period for Intravascular Stimulation In those dogs in which stimulation was performed at the superior vena cava and right pulmonary artery sites, the atrial and ventricular effective refractory periods and AV conduction during cardiac nerve stimulation were assessed. A—A intervals during parasympathetic stimulation at 40 V were measured in the right atrial appendage electrogram. The A—A intervals of 3 consecutive beats were taken for calculation of the mean A—A interval. Right atrial and right ventricular ERPs were determined at baseline and during cardiac nerve stimulation at the right pulmonary artery and superior vena cava sites by applying cardiac parasympathetic stimulation at an intensity of 40 V. For atrial and ventricular pacing, 2 ms rectangular pacing stimuli at twice the diastolic pacing threshold were delivered by a Radionics stimulator (Radionics, Inc., Burlington, Mass.) at the right atrial and the right ventricular pacing site using the extrastimulus technique. A train of 8 stimuli was delivered at a cycle length of 400 ms followed by a premature stimulus starting with a coupling interval of 350 ms. The premature stimulus was then decreased in 10 ms steps until no propagated response was observed in the surface ECG or the local intracardiac electrogram. The longest coupling interval $A_1$–$A_2$ ($V_r V_2$) of the premature beat that did not result in a propagated response was defined as the ERP at that stimulation site.

Long-term Stability of the Slowing Effect due to Parasympathetic Stimulation at the Coronary Sinus Long-term efficacy of cardiac nerve stimulation at the coronary sinus site was also evaluated. For this purpose, in an additional dog, continuous parasympathetic stimulation was maintained at a stimulus strength of 25 V over 20.5 hours during pacing induced atrial fibrillation. In this dog only, a left carotid arterial line and a right jugular access for introduction of the basket catheter were used. A thoracotomy was not performed. Every half hour the mean value of 10 consecutive R—R intervals during cardiac nerve stimulation was calculated. The stimulus voltage was then increased for 30 seconds to 39 V and another 10 consecutive R—R intervals were measured during this period. Both values were then compared to 10 consecutive R—R intervals during a 30-second stimulation pause.

Pharmacological Tests and Cervical Vagal Nerve Cutting

In one dog of each of the three study groups, 2 mg of atropine were injected intravenously and parasympathetic stimulation was attempted again. In another dog of each subgroup, both cervical vagal nerves were cut before parasympathetic stimulation was repeated. Also, in one dog of each study group, parasympathetic stimulation was repeated after topical application of 1% lidocaine on the outer surface of the proximal coronary sinus, close to the junction with the inferior vena cava.

Statistical Analysis

All data are expressed as mean±SD. In each group, repeated measure ANOVA was used to test whether the stimulus strength affected the ventricular rate during atrial fibrillation. The rate slowing effect at a given stimulus strength was compared to baseline values without parasympathetic stimulation applying a Wilcoxon matched pairs signed-rank test. In the dog in which a 20.5-hour measurement was performed, rate differences were compared using a Wilcoxon matched pairs signed-rank test. Refractory periods were evaluated for significance by means of a Student paired t-test. Probability values <0.05 were considered statistically significant.

EXAMPLE 2

Results of Parasympathetic Cardiac Nerve Stimulation

A) Parasympathetic Cardiac Nerve Stimulation in the Coronary Sinus

Figure 4:
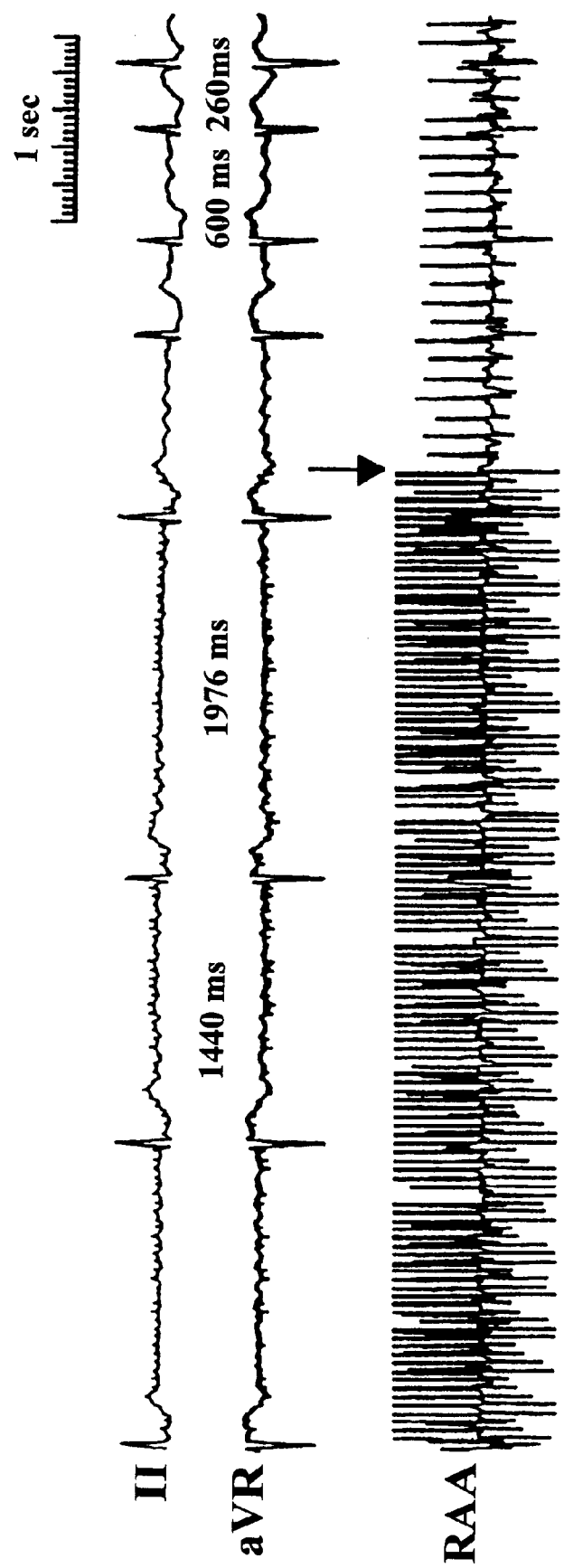
FIG. 4: Cardiac nerve stimulation (PS) in the coronary sinus (CS). Surface ECG lead II, aVR and a right atrial appendage (RAA) recording are depicted. Atrial fibrillation was induced and maintained by rapid pacing from the RAA at a cycle length of 100 ms (low frequency, low amplitude pacing artifacts on the right of the RAA-tracing). PS was done at a stimulus strength of 34 V and a frequency of 20 Hz (high frequency, high amplitude electrical artifacts can be seen on the left of the RAA-tracing). The cycle length values within the figure refer to the longest and shortest R—R interval during AF with PS (1976 and 1440 ms, respectively) and when PS was terminated (arrow, 600 and 260 ms, respectively).
Figure 5:
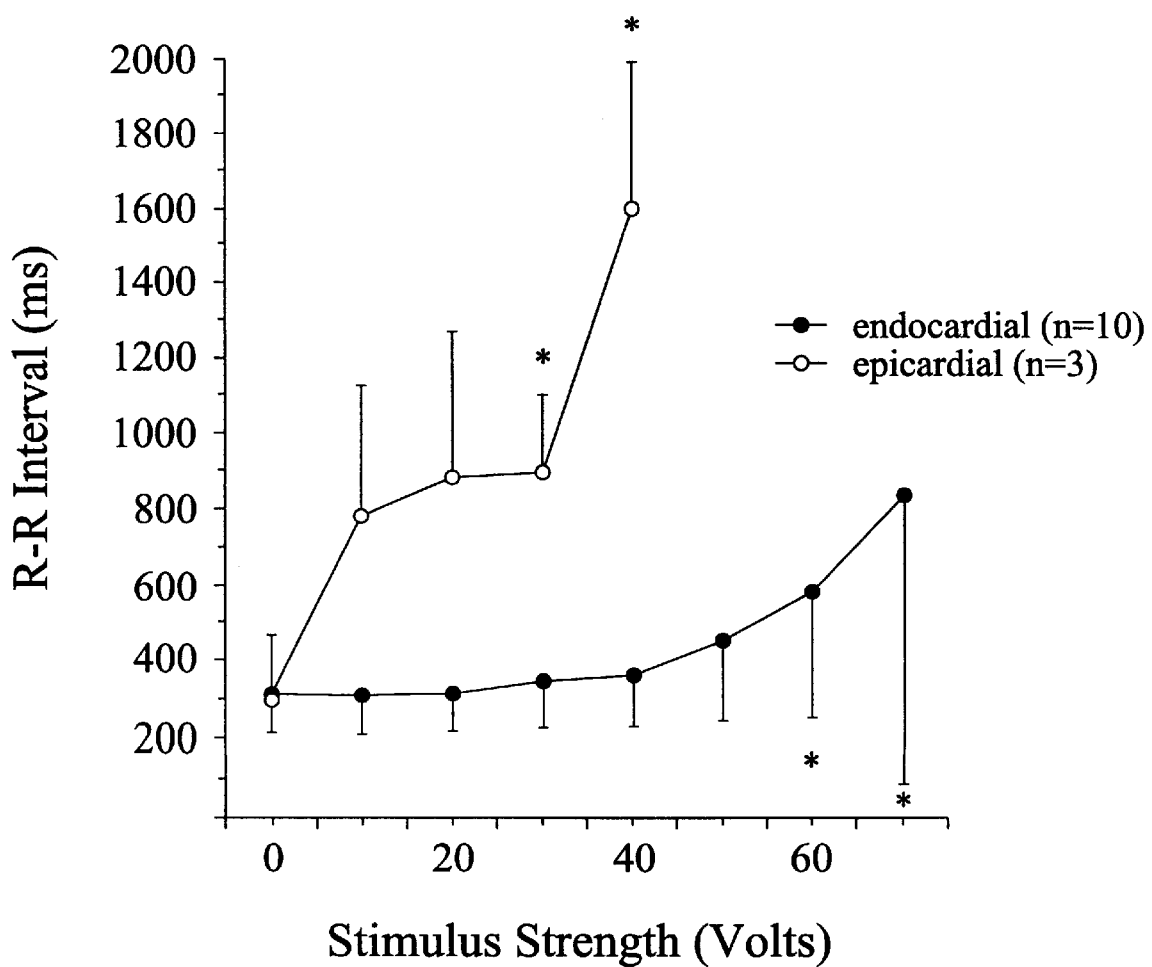
FIG. 5: Effect of stimulus strength (SST) on ventricular rate slowing during cardiac nerve stimulation (PS) in the coronary sinus. The average R—R interval during atrial fibrillation (AF) is plotted versus the SST. The SST significantly affected the R—R interval during AF ($p<0.001$, ANOVA). The mean R—R interval at each SST was also compared to the R—R interval without PS (*:$p<0.05$). Of note, during epicardial PS the threshold for a ventricular slowing effect during AF was considerably lower than during intravascular PS.

FIG. 4 shows a representative example of endovascular parasympathetic stimulation in the proximal coronary sinus. ECG leads II and aVR were recorded as well as an electrogram from the right atrial appendage. During parasympathetic stimulation with concomitantly induced atrial fibrillation, at 34 V and a frequency of 20 Hz, there was a marked increase of the R—R intervals (shortest 1440 ms, longest 1976 ms). Upon termination of parasympathetic stimulation (arrow), the longest and shortest R—R intervals were 600 and 260 ms, respectively. The lowest voltage at which at least a 50% increase of the R—R interval occurred during atrial fibrillation was 18±8 V (312±102 ms without parasympathetic stimulation vs. 561±172 ms during PS, p<0.001). The effect of the applied stimulus voltage on the magnitude of ventricular rate slowing was assessed by a dose-response curve as illustrated in FIG. 5. Stimulus strength significantly affected ventricular rate slowing during atrial fibrillation (p<0.001, ANOVA). The graph also shows that direct extravascular stimulation of the parasympathetic ganglia at the proximal coronary sinus region yielded a much lower parasympathetic stimulation threshold. Importantly, nerve stimulation from the epicardium during sinus rhythm with a hand held bipolar electrode effectively prolonged the AH interval without a change in the sinus rate but was subthreshold for stimulation of atrial myocardial tissue. By contrast, if nerve stimulation from the intravascular site was performed during sinus rhythm, it excited the atria, resulting in atrial fibrillation except in a few instances.

B. Parasymlpathetic Cardiac Nerve Stimulation in the Right Pulmonary Artery

Figure 6:
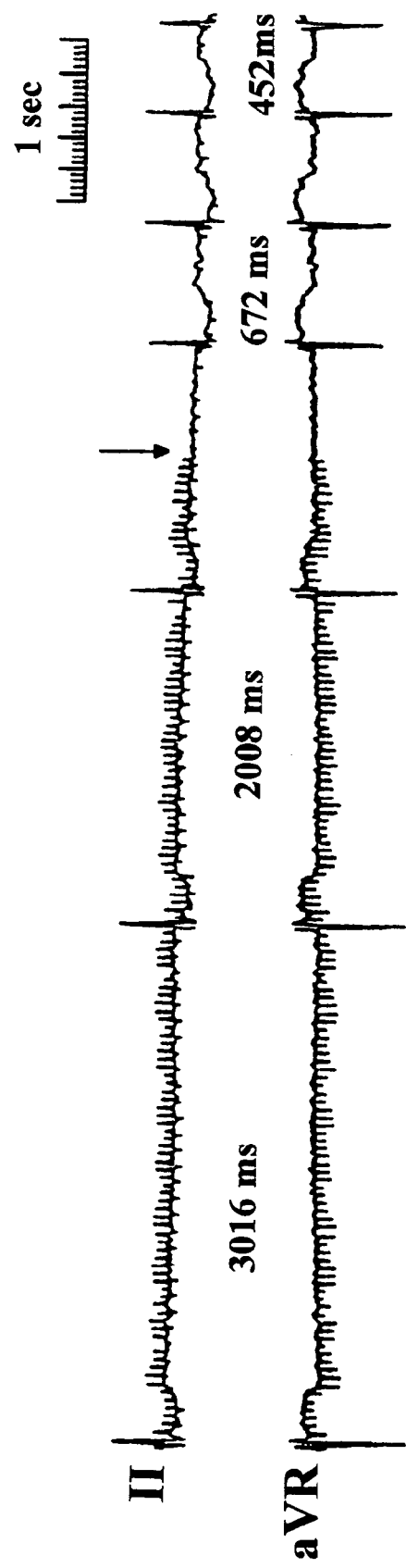
FIG. 6: Cardiac nerve stimulation in the right pulmonary artery. Surface ECG leads II and aVR are depicted. The offset of nerve stimulation is indicated by the vertical arrow. The electrical artifacts of cardiac nerve stimulation can be seen as higher voltage, high frequency signals on the left in the ECG tracings. The smaller pacing artifacts (cycle length 100 ms) for the induction and maintenance of atrial fibrillation (AF) are hidden by the nerve stimulation artifacts but can be seen after cessation of cardiac nerve stimulation (arrow). At a cardiac nerve stimulus intensity of 27 V (stimulus frequency: 20 Hz, stimulus duration: 0.05 ms) atrio-ventricular conduction during atrial fibrillation was substantially prolonged resulting in marked ventricular pauses (longest 3016 ms, shortest 2008 ms). After nerve stimulation was terminated, a rapid ventricular response (longest: 672 ms, shortest: 452 ms) resumed almost immediately.
Figure 7:
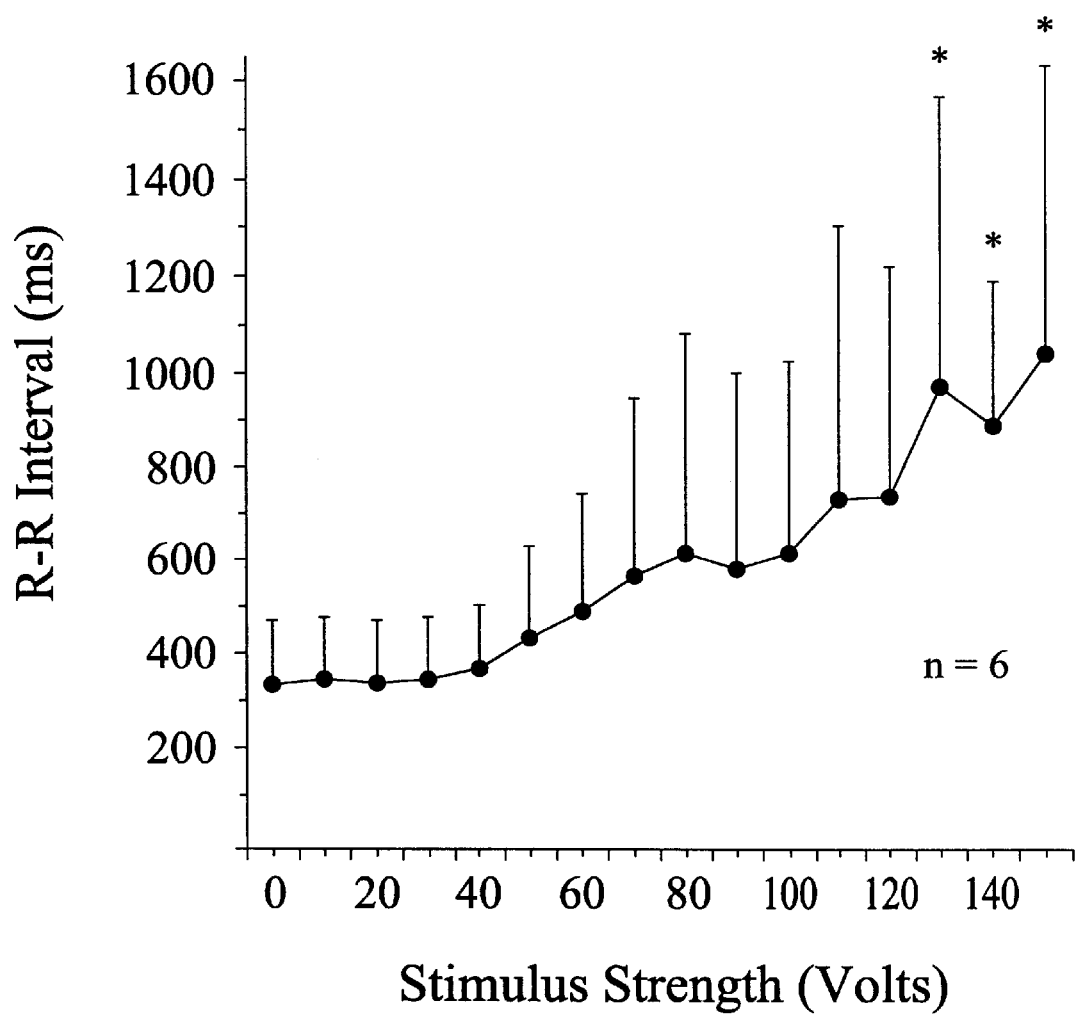
FIG. 7: Effect of stimulus strength (SST) on ventricular rate slowing during cardiac nerve stimulation (PS) in the right pulmonary artery (RPA). The average ventricular rate interval (R—R interval) during atrial fibrillation (AF) is shown on the ordinate whereas the abscissa represents the SST. With increasing SST the R—R interval during AF was lengthened ($p<0.001$, ANOVA). Individual values of the R—R interval at each SST were compared to the R—R interval without PS (*$p<0.05$).

Stimulation in the right pulmonary artery also decreased the ventricular rate response during atrial fibrillation as depicted in FIG. 6. During parasympathetic stimulation the largest R—R interval measured 3016 ms and the shortest 2008 ms whereas on termination of parasympathetic stimulation (arrow) the longest and shortest R—R intervals were 672 and 452 ms, respectively. The ventricular rate slowing effect depended on the stimulus strength (p<0.001, ANOVA). Increasing the stimulus strength led to a graded response of ventricular rate slowing during atrial fibrillation as shown in FIG. 6. The minimal stimulus strength inducing at least a 50% prolongation of the R—R interval during atrial fibrillation required 23±7 V (R—R interval of 307±62 ms without parasympathetic stimulation vs. 681±151 ms with parasympathetic stimulation, p<0.001). Stimulation in the right pulmonary artery also produced a shortening of the average right atrial refractory period (136±13 ms without parasympathetic stimulation vs. 96±22 ms during parasympathetic stimulation n=5, p=0.03) whereas the right ventricular refractory period did not change significantly with neural stimulation (184±25 ms with parasympathetic stimulation vs. 186±26 without parasympathetic stimulation, n±5). Moreover, a significant slowing of sinus rate was observed during stimulation at the right pulmonary artery site (1181±306 ms during parasympathetic stimulation vs. 518±138 ms without parasympathetic stimulation, n=6, p=0.01).

C. Parasympathetic Cardiac Nerve Stimulation in the Superior Vena Cava

Figure 8A:
FIG. 8A: Cardiac nerve stimulation in the superior vena cava (SVC). Surface ECG leads I, II and a VF and a recording of the stimuli (stim) delivered to the basket catheter are depicted. Atrial fibrillation was induced and maintained by rapid pacing from the RAA at a cycle length of 100 ms (low frequency, low amplitude electrical artifacts). The onset of parasympathetic nerve stimulation (PS) is indicated by a vertical arrow. At a PS intensity of 13 V (stimulus frequency of 20 Hz, the shortest R—R interval during atrial fibrillation prolonged from 352 ms to 384 ms and the longest R—R interval from 408 to 1464 ms.
Figure 8B:
FIG. 8B: Increasing the stimulus amplitude to 27 V led to an even greater increase of the R—R intervals (shortest: 272 ms to 1008 ms; longest: 380 ms to 2336 ms). The onset of parasympathetic stimulation is indicated by vertical arrow.
Figure 9:
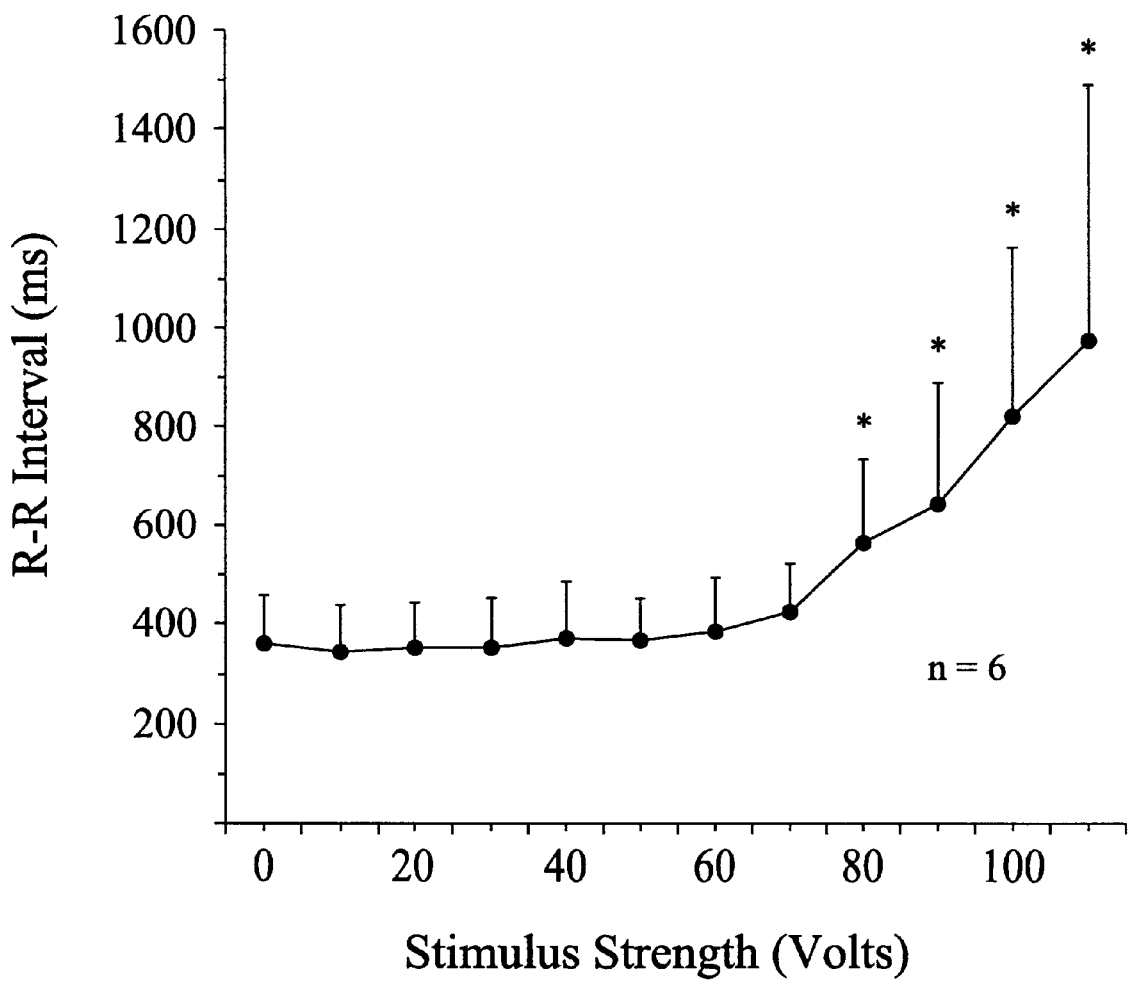
FIG. 9: Effect of stimulus strength (SST) on ventricular rate slowing during cardiac nerve stimulation (PS) in the superior vena cava (SVC). The average ventricular rate interval (R—R interval) during atrial fibrillation (AF) is shown on the ordinate whereas the abscissa represents the SST. A substantial prolongation of the R—R interval with increasing SST was observed ($p<0.001$, ANOVA). Individual values of the R—R interval at each SST were compared to the R—R interval without PS (*$P<0.05$).

A sufficient ventricular rate slowing during atrial fibrillation was also observed during parasympathetic stimulation in the proximal SVC. A typical example is shown in FIG. 8A. At the onset of parasympathetic stimulation (arrow, stimulus strength of 13 V) the longest and shortest R—R intervals measured were 1464 and 384 ms, respectively, compared to baseline values of 408 and 352 ms. During parasympathetic stimulation at a stimulus strength of 22 V (arrow, FIG. 8B), these values increased to 2336 and 1008 ms. The lowest voltage at which a 50% increase of the mean ventricular cycle length during atrial fibrillation occurred was 25+11 V (331±139 ms without parasympathetic stimulation vs. 653±286 ms during parasympathetic stimulation, p<0.001). The stimulus strength during parasympathetic stimulation significantly affected the ventricular rate during atrial fibrillation as illustrated by FIG. 9 (p<0.001, ANOVA). During sinus rhythm, maximal cardiac nerve stimulation led to a significant increase in the average sinus cycle length (489±154 ms without parasympathetic stimulation vs. 1056±355 ms with PS, n=6, p<0.001) and to a shortening of the right atrial refractory period (145±55 ms without parasympathetic stimulation vs. 78±71 ms with PS, n=6, p=0.03). The right ventricular refractory period did not change significantly during parasympathetic stimulation (172±26 ms with parasympathetic stimulation vs. 176±34 ms without parasympathetic stimulation, n=5). Intermittent stimulation of the phrenic nerve was sometimes observed during stimulation across various splines of the electrode basket catheter. When the site and electrode pair was found at which electrical stimulation induced ventricular slowing during atrial fibrillation, stimulation of the phrenic nerve was never observed.

D. Effect of Different Nerve Stimulation Algorithms

Stimulation in the coronary sinus during sinus rhythm in most instances resulted in local atrial tissue capture, thereby inducing atrial fibrillation at a voltage that was lower than the one which resulted in ventricular rate slowing during atrial fibrillation. However, stimulation in the right pulmonary artery or superior vena cava did not capture any myocardial tissue.

Therefore, another algorithm for parasympathetic stimulation at the coronary sinus site was tested: trains of stimuli (stimulus frequency: 200 Hz) each lasting 10 ms were delivered at a train rate of 200/min (cycle length=300 ms). These pulsed trains also excited atrial tissue, resulting in atrial pacing at a rate of 200/min. Importantly, 2:1 AV block was observed during these episodes. Without pulsed parasympathetic stimulation but with pacing from the right atrial appendage site at a rate of 200/min, no AV block was present.

Figure 10A:
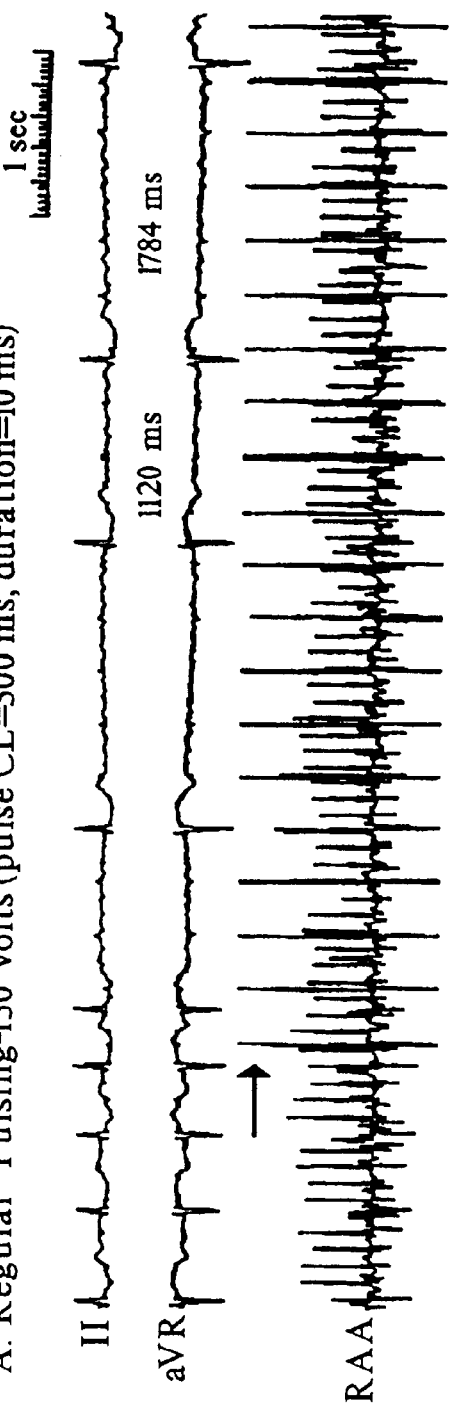
FIG. 10A: Effect of intermittent cardiac nerve stimulation on atrioventricular conduction during atrial fibrillation. Surface ECG lead II and aVR and an epicardial recording from the right atrial appendage (RAA) are shown. Trains of 200 Hz stimuli, each lasting 10 ms were delivered at a train rate of 200/min. These trains can be seen as large regular electrical artifacts in the right atrial appendage (RAA) recording. atrial fibrillation (AF) was induced and maintained with rapid atrial pacing (cycle length 100 ms, high frequency, low amplitude pacing artifacts in the RAA recording). The onset of nerve stimulation is indicated by a horizontal arrow in the RAA tracing. At a stimulus strength of 34 V, intermittent, regular nerve stimulation markedly reduced the ventricular response during atrial fibrillation (longest R—R=1784 ms; shortest R—R=1120 ms).
Figure 10B:
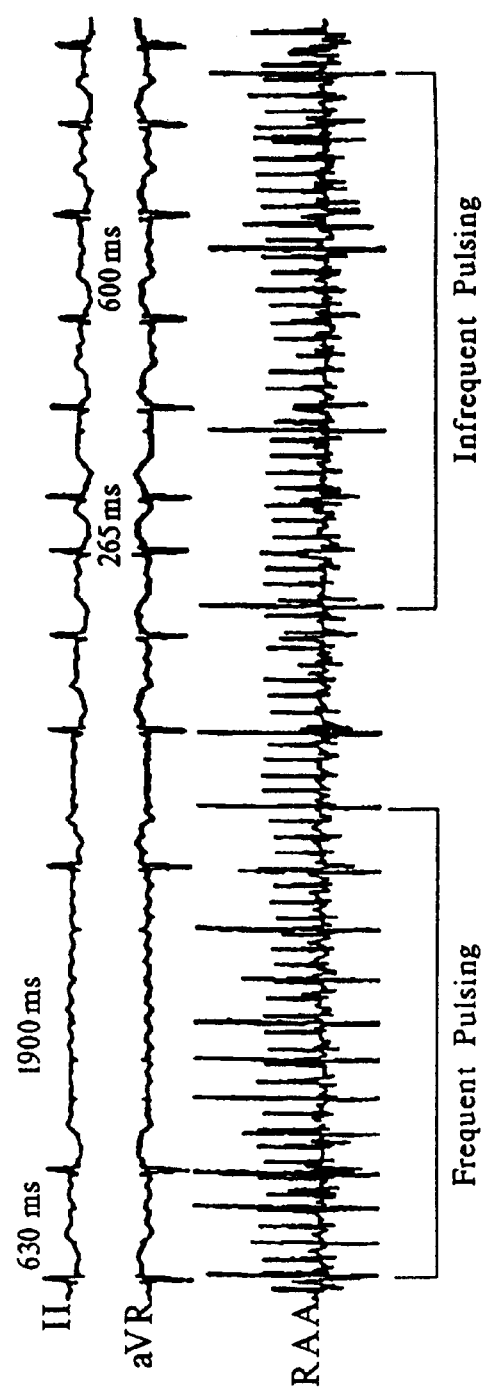
FIG. 10B: This negative dromotropic effect depended on the train rate. At the beginning, trains were delivered at a shorter but irregular cycle length (frequent pulsing) resulting in a notable ventricular rate slowing during atrial fibrillation (longest R—R=1900 ms; shortest R—R=630 ms). When the pulsing rate became infrequent and irregular (right side of the recording), the ventricular rate slowing effect during atrial fibrillation was considerably less (longest R—R=600 ms; shortest R—R=265 ms).

The efficacy of intermittent stimulation trains to slow the ventricular rate during atrial fibrillation is illustrated in FIG. 10. At a stimulus strength of 34 V, intermittent pulses of parasympathetic stimulation (constant train cycle length of 300 ms, train duration 10 ms) markedly reduced the ventricular response during atrial fibrillation. A negative dromotropic effect was also achieved when the trains of stimuli were delivered irregularly as demonstrated in FIG. 10B. At the beginning of the recordings trains with frequent pulsing but irregular train cycle length resulted in a notable ventricular cycle length prolongation (1900 ms longest, 630 ms shortest) during atrial fibrillation. When the pulsing was infrequent and irregular (right side of the tracings), the ventricular cycle length prolongation during atrial fibrillation was not as great (600 ms longest, 265 ms shortest).

Increasing the train cycle length from 300 ms to 500 ms at a train duration of 10 ms led to a decrease of the ventricular rate slowing effect during parasympathetic stimulation at 34 V (average ventricular cycle length of 2105±1160 ms at a train cycle length of 300 ms vs. 942±294 ms at a train cycle length of 500 ms vs. 379±65 ms without parasympathetic stimulation, n=2). The rate slowing effect also depended on the train duration as found in another 2 dogs: at a constant train cycle length of 300 ms, the decrease in average ventricular cycle length during atrial fibrillation was higher for trains lasting 100 ms 13 (1325±663 ms, SST; 150 V) than for trains with a duration of 10 ms (1156±566 ms, SST: 150 V vs. 474±91 ms without parasympathetic stimulation, n=2).

Figure 11:
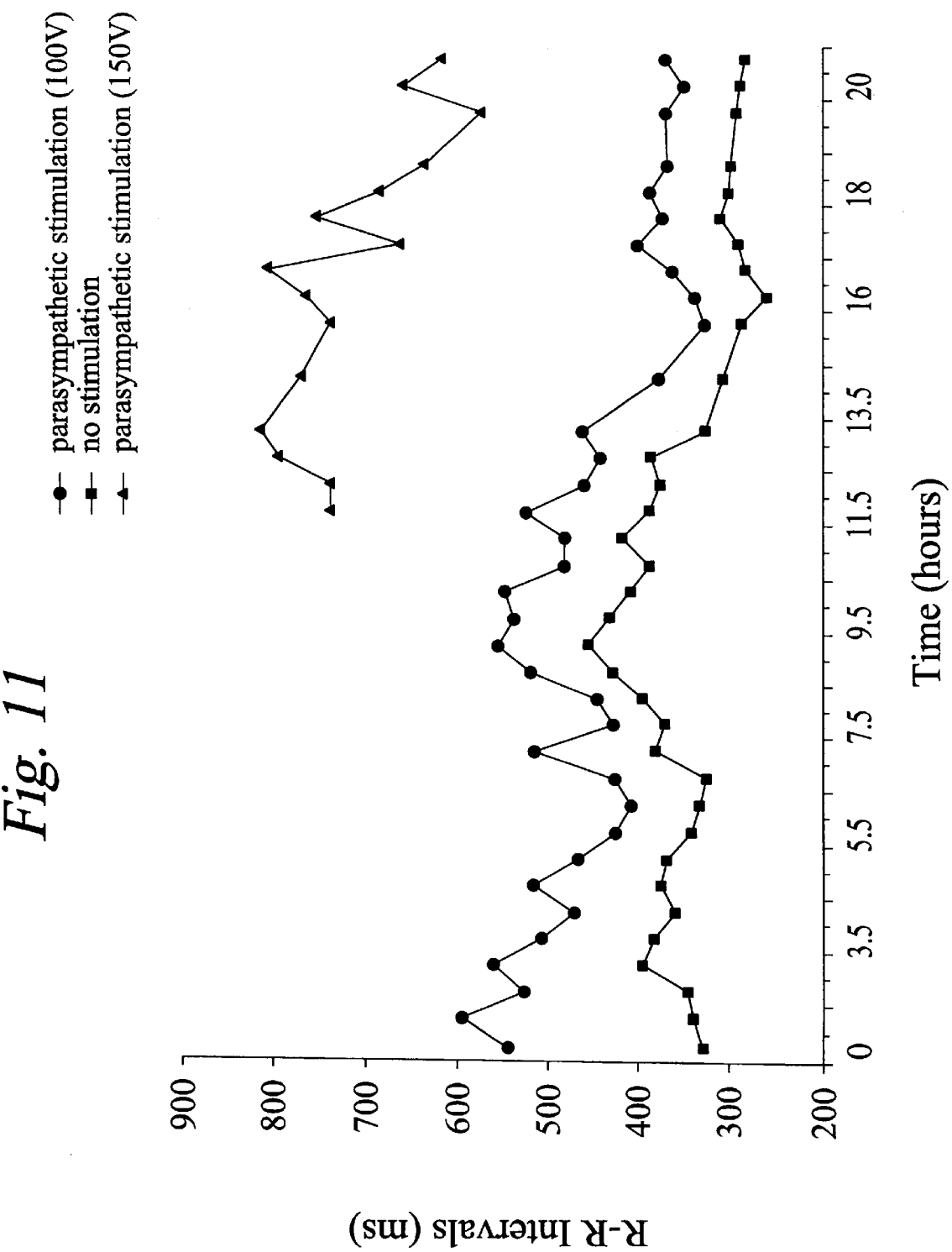
FIG. 11: Continuous parasympathetic cardiac nerve stimulation in the coronary sinus over 20.5 hours. The ventricular rate (R—R interval) during atrial fibrillation (AF) is plotted versus time. After a slight decrease of the rate slowing effect during the initial 2 hours the rate slowing effect persisted over the remaining 20.5 hours. There was always a reserve of the negative dromotropic effect as demonstrated by a further prolongation of the R—R interval when the stimulus voltage was intermittently increased from 25 to 39 V.

E. Long-term Stability of the Slowing Effect due to Parasympathetic Stimulation at the Coronary Sinus To test if there was a fading of the slowing effect during a longer stimulation period, continuous nerve stimulation in the coronary sinus was performed over 2 hours in 2 dogs. Although the mean R—R interval during atrial fibrillation after 2 hours of parasympathetic stimulation was shorter than at the onset of parasympathetic stimulation (644±149 ms vs. 778 ±210 ms, n=2), it was still longer compared to the R—R intervals without parasympathetic stimulation (452±114 ms, n=2). In another dog, the stability of the rate slowing effect was assessed over a 20.5-hour period as illustrated in FIG. 11. The effect of ventricular rate slowing during atrial fibrillation slightly decreased over the 20.5-hour period of parasympathetic stimulation. However, after 20.5 hours there was still a considerable decrease of the ventricular rate during parasympathetic stimulation as compared to no parasympathetic stimulation. The latter was determined during a 30 s period of no parasympathetic stimulation. Of note, this small loss of efficacy over 20.5 hours was overcome if the stimulus strength was increased from 36 V to 39 V as shown in FIG. 11.

F. Pharmacological Procedures and Cutting of the Cervical Vagal Nerves

At all three stimulation sites, the effect of parasympathetic stimulation on the ventricular response during atrial fibrillation was completely abolished after intravenous injection of 2 mg of atropine. Similarly, local extravascular application of lidocaine (to block nerve conduction) on the proximal coronary sinus close to the junction of the inferior vena cava and right atrium prevented the ventricular rate slowing effect during parasympathetic stimulation in the right pulmonary artery, superior vena cava and coronary sinus. By contrast, cutting both cervical vagal nerves did not change the parasympathetic stimulation related decrease of the ventricular response during atrial fibrillation at any of the 3 stimulation sites.

G. Comparison of Various Sites for Parasympathetic Stimulation

Although a sufficient ventricular rate reduction was consistently achieved at each stimulation site, there are specific characteristics of each location which may influence the choice of sites for use in individual patients. Placement of an electrode catheter without a deflectable tip in the coronary sinus through jugular or subclavian venous access is a standard procedure during electrophysiological procedures in patients. Similarly, introduction of the basket catheter in the coronary sinus was achieved by a transvenous access in our study. However, because this approach may require some technical experience, entrance to the right pulmonary artery may be more readily achieved in individual patients. This is because most physicians may be more confident doing pulmonary catheterization, which is a standard procedure during evaluation of valvular or congestive heart disease, than coronary sinus catheterization. However, both the coronary sinus and the right pulmonary artery approach can be used with a fluoroscopy to position the catheter. On the other hand, the superior vena cava site was reached without fluoroscopy in the Examples, making this approach more suitable for an acute emergency situation in critically ill patients.

A limitation of continuous stimulation at the coronary sinus site is that effective parasympathetic stimulation may result in electrical excitation of atrial tissue. Although this is not relevant in the setting of chronic atrial fibrillation, it may contribute to the perpetuation of atrial fibrillation in patients with recent onset atrial fibrillation. An algorithm consisting of repetitive trains of stimuli has proved to be efficacious in slowing the heart rate during atrial fibrillation. The negative dromotropic effects were higher with more frequent or longer duration trains. Therefore, one can couple trains of stimuli to the QRS complex during atrial fibrillation to result in an automatic adjustment of the intensity of parasympathetic stimulation to the ventricular rate during atrial fibrillation. Moreover, in case of termination of atrial fibrillation, ongoing train delivery may only evoke atrial extrasystoles that are coupled to the QRS complex and may not reinduce atrial fibrillation.

Once the catheter was positioned at any of the three stimulation sites and the basket was expanded, no dislocation of the catheter was observed. Theoretically, in case of dislocation of the stimulating catheter in the coronary sinus or right pulmonary artery catheter in the right ventricle, induction of ventricular fibrillation might occur if a continuous stimulation algorithm is applied. This may be avoided by delivering trains of parasympathetic stimuli during the absolute ventricular refractory period which could be achieved by triggered delivery of the trains immediately after the end of the QRS complex.

EXAMPLE 3

Ablation of Parasympathetic Nerves

A. Ablation at the Junction of the Superior Vena Cava and Right Atrium Terrninates Neurally Induced Atrial Fibrillation.

Atrial tissue at the junction of the superior vena cava (SVC) and right atrium (RA) has been implicated as the source for symptomatic atrial tachycardia and atrial fibrillation. Here, eight dogs were anesthetized with sodium pentobarbital, and had a basket catheter of the invention expanded at the SVC/RA junction for bipolar recording and pacing. Atrial electrograms were also recorded from close bipolar electrodes at the right atrium and left atrial appendage, along Bachmann's bundle, coronary sinus and the pulmonary veins. In order to avoid atrial activation during nerve stimulation, the right atrium was paced at a rate of either 150/min or 330/min with each pacing stimulus coupled (20 msec) to a 50 msec train of high frequency stimuli (200 Hz, each stimulus lasting 0.1 msec). Voltages for neural stimulation trains were titrated from 2–40 V.

At an average of 23±4V (mean±std. dev.), rapid atrial tachycardia leading to atrial fibrillation was induced which was characterized by early activation and continuous electrical activity in the vicinity of the SVC. At significantly lower voltages (17±6 V, p=0.02), concealed atrial ectopic beats were recorded with occasional firing from the SVC area showing exit block to the rest of the atria. With beta-blockade (esmolol, 1 mg/kg, n=4), the atrial fibrillation threshold increased to 28±6 V (n=3, p=0.04). In one dog, atrial fibrillation was no longer inducible after esmolol injection. Atropine (2 mg, n=3) completely abolished stimulation induced atrial premature beats, atrial tachycardia, and atrial fibrillation. Two to four hours after autonomic blockade, the stimulation induced arrhythmias returned. Radiofrequency current (70V, impedance 180–220 ohms, 60 sec, n=8) again completely abolished the induction of atrial premature beats, atrial tachycardia and atrial fibrillation, even at the highest voltage (39 V). The average number of radiofrequency current ablations needed to achieve these results was 2.9±1.6/dog.

The SVC/RA junction appears to be a site for neurally induced atrial premature beats, atrial tachycardia and atrial fibrillation which can be abolished by autonomic blockade or electrical ablation of parasympathetic atrial innervation. Ablation may destroy the atrial myocardium which is the source of the arrhythmias or the adjacent neural elements or both.

B. Ablation at the Inferior Vena Cava and Right Pulmonary Artery Abolishes Vagal Atrial Fibrillation The parasympathetic nervous system considerably shortens the atrial refractory period and can maintain atrial fibrillation. We demonstrated that intravascular radiofrequency catheter ablation of the parasympathetic nerves innervation the atria can be achieved and prevents electrically induced atrial fibrillation which was maintained by supramaximal bilateral cervical vagal nerve stimulation (VNS).

In six dogs, intravascular atrial denervation (IAD) was performed using intravascular radiofrequency current ablation of parasympathetic atrial nerves in the right pulmonary artery and inferior vena cava. Atrial fibrillation was induced with rapid atrial stimulation and maintained by VNS. Before and after IAD, the product of conduction velocity and atrial refractory period (AERP) was determined at seven atrial sites (high and low right atrium, proximal and distal coronary sinus and Bachmann bundle, left superior pulmonary vein) at baseline and during VNS. Before LAD, AERPs shortened from 124±5 ms at baseline to 40±7 ms during VNS (p<0.001). At all seven atrial sites, atrial fibrillation could be induced and maintained by rapid atrial stimulation and VNS. After IAD, vagally induced shortening of the AERPs was considerably blunted (125±3 ms at baseline to 116±5 ms during VNS, p=0.01). After lAD, atrial fibrillation could not longer be induced and maintained by rapid atrial stimulation and VNS at any of the seven atrial sites. No intravascular thrombi or vessel perforation were observed after ablation.

The description and Examples herein show for the first time a transvenous approach to stable and consistent acute and long term parasympathetic cardiac nerve stimulation. Using the stimulation method and catheter of the invention, it has been shown that the negative dromotropic effect during intravascular coronary sinus stimulation is sufficient to cause a considerable ventricular rate slowing during atrial fibrillation. The use of the basket catheter allows rapid, consistent, and stable electrode placement at the desired site, even over long time periods. A negative dromotropic effect can also be achieved during intravascular stimulation in the superior vena cava or right pulmonary artery. In addition to a negative dromotropic effect, a negative chronotropic effect and a shortening of the atrial refractory period can be achieved in the superior vena cava and right pulmonary artery.

The system and method of the invention provide means to stimulate autonomic neurons innervating the heart from within the vasculature to regulate atrial and/or ventricular function. Beneficial results are achieved by significant supraventricular and ventricular rate slowing. Such treatment is particularly useful to counteract undesirable positive chronotropic effects of catecholamines during treatment of cardiogenic or septic shock, acute congestive heart failure, or in patients with rapid ventricular response during atrial fibrillation and poor left ventricular function who are not good candidates for beta blockers or calcium channel antagonists. Additionally, autonomic nerve stimulation or selective ablation is useful in patients with conditions such as paroxysmal atrial fibrillation and symptomatic atrial tachycardia and fibrillation. The disclosed methods are superior to previously reported stimulation methods to correct tachycardia because they do not require surgical entry into the thoracic cavity, and do not require ablation of muscle.

The preceding description has been presented with references to presently preferred embodiments of the invention. Persons skilled in the art and technology to which this invention pertains will appreciate that alterations and changes in the described structures and methods can be practiced without meaningfully departing from the principle, spirit and scope of this invention.

Accordingly, the foregoing description should not be read as pertaining only to the precise structures and methods described and shown in the accompanying drawings, but rather should be read as consistent with and as support for the following claims, which are to have their fullest and fairest scope.

References

1. Prystowsky E N, Benson D W, Fuster V, Hart R G, Neal Kay G N, Myerburg R J, Naccarelli G V, Wyse D G. Management of patients with atrial fibrillation: A statement for healthcare professionals from the subcommittee on electrocardiography and electrophysiology, American Heart Association. Circulation 1996;93:1262–1277
2. Wolf P A, Abbott R D, Kannel W B. Atrial fibrillation as an independent risk factor for stroke: the Framingham Study. Stroke 1991 ;22:983–988
3. Kannel W B, Abbott R D, Savage D D, McNamara P M. Epidemiologic features of chronic atrial fibrillation: The Framingham Study. N Engl J Med 1982; 306:1018–22
4. Benjamin E J, Levy D, Vazin S M et al. Independent risk factors for atrial fibrillation in a population-based cohort. JAMA 1994;271:840–844
5. Van Gelder I C, Crijns H J. Cardioversion of atrial fibrillation and subsequent maintenance of sinus rhythm. Pacing Clin Electrophysiol 1997; 20 (10,2): 2675–2683
6. Brodsky M A, Allen B J, Walker C J, et al. Amiodarone for maintenance of sinus rhythm after conversion of atrial fibrillation in the setting of dilated left atrium. Am J Cardiol 1987;60:572–575
7. Myerburg R J, Castellanos A. Cardiac arrest and sudden death. In: Braunwald E, ed. Heart disease: A textbook of cardiovascular medicine, 4th edition, Philadelphia, W B Saunders 1992:756–789.
8. Vanoli E, De Ferrari G M, Stramba-Badiale M et al. Vagal stimulation and prevention of sudden death in concious dogs with a healed myocardial infarction. Circ Res 1991;68:1008–1014.
9. Puddu P E, Jouve R, Langlet F et al. Prevention of postischemic ventricular fibrillation late after right or left stellate ganglionectomy in dogs. Circulation 1988;77:935–946.
10. Lazzara R, Scherlag B J, Robinson M J et al. Selective in situ parasympathetic control of the canine sinuatrial and atrioventricular node. Circ Res 1973; 32:393–401
11. Chen S A, Chiang C E, Tai C T et al. Intracardiac stimulation of human parasympathetic nerve fibers induces negative dromotropic effects: implication with the lesions of radiofrequency catheter ablation. Cardiovasc Electrophysiol. 1998;9: 245–252
12. Reek S, Geller J C, Hartung W M, Auricchio A. Einfluss transvenöser elektrischer Stimulation in der rechten Pulmonalarterie auf Sinusknotenläre und ventrikulare Refraktärzeiten. Z Kardiologie 1999;88, Suppl 1:10
13. Murphy D A, Johnstone D E, Armour J A. Preliminary observations on the effects of stimulation of cardiac nerves in man. Can J Physiol Pharmacol. 1985;63:649–655
14. Quan K J, Mackall J A, Biblo L A, Van Hare G F, Carlson M D. Endocardial parasympathic stimulation slows the ventricular rate during atrial fibrillation in humans. PACE 1996;19:647 (abstract)
15. Chiou C W, Eble J N, Zipes D P. Efferent vagal innervation of the canine atria and sinus and atrioventricular nodes. Circulation 1997;95:2573–2584
16. Thompson G W, Levett J M, Miller S M et al. Bradycardia induced by intravascular versus direct stimulation of the vagus nerve. Ann Thorac Surg 1998;65(3):637–42
17. Coumel P et al. Syndrome d'arythmie auriculaire d'origine vagale. Arch Mal Coeur 1978;71:645–656.

What is claimed is:

1. A method of regulating the heart rate of a patient comprising:
   inserting an electrophysiology catheter having a tip section with at least one stimulating electrode into a blood vessel and directing the catheter to an intravascular location wherein the at least one stimulating electrode of the catheter is adjacent a selected cardiac sympathetic or parasympathetic nerve;
   stabilizing the at least one electrode at said intravascular location; and
   delivering a stimulus through the at least one electrode, said stimulus selected to stimulate the adjacent sympathetic or parasympathetic nerve to thereby cause a regulation of the patient's heart rate.

2. The method of claim 1 wherein the stimulation causes a slowing of the heart rate.

3. The method of claim 2 wherein the patient is suffering from atrial or ventricular tachycardia.

4. The method of claim 2 wherein the patient is suffering from atrial flutter.

5. The method of claim 2 wherein the patient is suffering from atrial fibrillation.

6. The method of claim 1 wherein the intravascular location is selected from the group consisting of coronary sinus, right pulmonary artery, and superior vena cava.

7. The method of claim 1 wherein the catheter is steerable.

8. A method as claimed in claim 1 wherein the catheter comprises
   an elongated catheter body having proximal and distal ends and at least one lumen theretlrough;
   a tip section comprising a section of flexible tubing having proximal and distal ends and at least one lumen therethrough, the proximal end of said tubing being fixedly attached to the distal end of the catheter body, said tip section further comprising a basket assembly at the distal end of the flexible tubing, said basket assembly comprising a plurality of arms connected at their proximal and distal ends, each arm comprising at least one electrode, said basket assembly having an expanded arrangement wherein the arms bow radially outwardly and a collapsed arrangement wherein the arms are arranged generally along the axis of the catheter tip section; and
   wherein at least one arm comprises the at least one stimulating electrode.

9. A method as claimed in claim 8 wherein the at least one stimulating electrode is stabilized at said intravascular location by expanding the basket assembly at that intravascular location.

10. The method of claim 9 wherein the diameter of the basket assembly in its expanded arrangement is no more than about 30 mm and the length of the basket assembly in its expanded arrangement is no more than about 60 mm.

11. A method as claimed in claim 9 wherein the length of the basket assembly in its expanded arrangement is from about 20 to about 40 mm.

12. A method as claimed in claim 11 wherein the diameter of the basket assembly in its expanded arrangement is from about 10 mm to about 15 mm.

13. The method of claim 1 wherein the stimulus comprises one or more electrical signals having a frequency of from about 1 Hz to about 200 Hz, an intensity of from about 1V to about 150V and a duration of from about 0.01 msec to about 10 msec.

14. The method of claim 13 wherein the frequency of the electrical signal(s) is between about 20 Hz to about 30 Hz.

15. The method of claim 13 wherein the intensity of the electrical signal(s) is from about 8V to about 15V.

16. The method of claim 13 wherein the duration of the electrical signal(s) is from about 0.05 msec to about 0.1 msec.

17. The method of claim 1 wherein the stimulation is timed to occur during a myocardial refractory period.

18. The method of claim 17 wherein the refractory period is regulated by myocardial pacing.

19. The method of claim 18 wherein the myocardial pacing is elicited from the stimulating electrode or a second electrode on the catheter.

20. The method of claim 1 wherein the nerve is primarily parasympathetic.

21. The method of claim 1 wherein the nerve is primarily sympathetic.

22. A method of regulating the heart rate of a patient comprising: providing an electrophysiological catheter comprising:
   an elongated catheter body having proximal and distal ends and at least one lumen therethrough;
   a tip section comprising a section of flexible tubing having proximal and distal ends and at least one lumen therethrough, the proximal end of said tubing being fixedly attached to the distal end of the catheter body, said tip section further comprising a basket assembly at the distal end of the flexible tubing, said basket assembly comprising a plurality of arms connected at their proximal and distal ends, each arm comprising at least one electrode, said basket assembly having an expanded arrangement wherein the arms bow radially outwardly and a collapsed arrangement wherein the arms are arranged generally along the axis of the catheter tip section;
   inserting the catheter into a blood vessel and directing the catheter to an intravascular location, wherein the at least one electrode of basket assembly is adjacent a selected cardiac sympathetic or parasympathetic nerve;

expanding the basket assembly to stabilize the at least one electrode adjacent the selected cardiac sympathetic or parasympathetic nerve; and delivering a stimulus through the at least one adjacent electrode, said stimulus selected to stimulate the adjacent sympathetic or parasympathetic nerve to thereby cause a regulation of the patient's heart rate.

23. The method of claim 22 wherein the stimulation causes a slowing of the heart rate.

24. The method of claim 23 wherein the patient is suffering from atrial or ventricular tachycardia.

25. The method of claim 22 wherein the patient is suffering from atrial flutter.

26. The method of claim 22 wherein the patient is suffering from atrial fibrillation.

27. The method of claim 22 wherein the intravascular location is selected from the group consisting of coronary sinus, right pulmonary artery, and superior vena cava.

28. The method of claim 1 wherein the catheter is steerable.

29. The method of claim 22 wherein the diameter of the basket assembly in its expanded arrangement is no more than about 30 mm and the length of the basket assembly in its expanded arrangement is no more than about 60 mm.

30. The method of claim 29 wherein the length of the basket assembly in its expanded arrangement is from about 20 to about 40 mm.

31. A method as claimed in claim 30 wherein the diameter of the basket assembly in its expanded arrangement is from about 15 mm to about 28 mm.

32. The method of claim 22 wherein the stimulus comprises one or more electrical signals having a frequency of from about 1 Hz to about 200 Hz, an intensity of from about 1V to about 200 V and a duration of from about 0.01 msec to about 10 msec.

33. The method of claim 32 wherein the frequency of the electrical signal(s) is about 20 Hz to about 30 Hz.

34. The method of claim 32 wherein the intensity of the electrical signal(s) is from about 8V to about 15V.

35. The method of claim 32 wherein the duration of the electrical signal(s) is about 0.05 msec to about 0.1 msec.

36. The method of claim 22 wherein the stimulation is timed to occur during a myocardial refractory period.

37. The method of claim 38 wherein the refractory period is regulated by myocardial pacing.

38. The method of claim 37 wherein the myocardial pacing is elicited from the stimulating electrode or a second electrode on the catheter.

39. The method of claim 22 wherein the nerve is primarily parasympathetic.

40. The method of claim 22 wherein the nerve is primarily sympathetic.

41. A method of selectively ablating a sympathetic or parasympathetic innervation of at least one portion of the heart of a patient comprising:

inserting an electrophysiological catheter having a tip section with an ablation electrode into a blood vessel and directing the catheter to an intravascular location wherein the ablation electrode of the catheter is adjacent to a selected sympathetic or parasympathetic nerve;

stabilizing the ablation electrode at said intravascular location;

delivering an ablation stimulus through the electrode, said ablating stimulus being sufficient to damage the nerve so that it no longer conducts impulses to the heart.

42. The method of claim 41 wherein the ablating stimulus comprises a radiofrequency stimulus.

43. The method of claim 41 wherein the ablating stimulus comprises a cryoablation stimulus.

44. A system to regulate the heart rate of a patient comprising:

a) a catheter having:

an elongated catheter body, the body having proximal and distal ends and at least one lumen therethrough;

a tip section comprising a section of flexible tubing having proximal and distal ends and at least one lumen therethrough, the proximal end of said tubing being fixedly attached to the distal end of the catheter body, said tip section further comprising a basket assembly at the distal end of the flexible tubing, said basket assembly comprising a plurality of arms connected at their proximal and distal ends, each arm comprising at least one electrode, said basket assembly having an expanded arrangement wherein the arms bow radially outwardly and a collapsed arrangement wherein the arms are arranged generally along the axis of the catheter tip section, the length of the basket assembly in its expanded arrangement being from about 20 to about 60 mm; and b) a pulse generator electrically connected to the at least one electrode in each arm of the basket assembly, said pulse generator capable of generating stimulating pulses having a frequency of from about 1 Hz to about 200 Hz, an intensity of from about 1V to about 200 V and a duration of from about 0.01 msec to about 10 msec.

45. The system of claim 44 wherein the length of basket assembly in its expanded arrangement is from about 20 to about 40 mm.

46. The system of claim 44 wherein the diameter of the basket assembly in its expanded arrangement is from about 10 to about 30 mm.

47. The system of claim 45 wherein the diameter of the basket assembly in its expanded arrangement is from about 10 to about 20 mm.

48. The system of claim 44 wherein the frequency of the stimulating pulses is between about 20 Hz to about 30 Hz, the intensity of the electrical signal(s) is between about 8V to about 15V, and the duration of the electrical signal(s) is from about 0.05 msec to about 0.1 msec.

49. The system of claim 44 further comprising a heart rate monitor for monitoring the heart rate of a patient.

50. The system of claim 49 further comprising a display for displaying the monitored heart rate of a patient.

51. The system of claim 49 further comprising a programmable controller electrically connected to the pulse generator and to the heart rate monitor, said controller programmed to activate the pulse generator to transmit a select stimulating pulse sequentially to each of the at least one electrode of each basket assembly arm after the catheter has been inserted into a blood vessel of a patient and placed at an intravascular location adjacent a sympathetic or parasympathetic nerve to be stimulated and for determining which of the at least one electrodes are closest to the nerve to be stimulated.

52. The system of claim 51 wherein the controller is further programmed to, once the at least one electrode nearest the nerve to be stimulated has been determined, activate the pulse generator to transmit a stimulating signal to said nearest at least one electrode and to vary one or more of the intensity, frequency, and pulse duration of said stimulating signal to obtain a select reduction in the heart beat rate of the patient.

53. A catheter for use in regulating the heart rate of a patient comprising:

an elongated catheter body, the body having proximal and distal ends and at least one lumen therethrough;

a tip section comprising a section of flexible tubing having proximal and distal ends and at least two lumens therethrough, at least one such lumen being off-axis, the proximal end of said tubing being fixedly attached to the distal end of the catheter body, said tip section further comprising a basket assembly at the distal end of the flexible tubing, said basket assembly comprising a plurality of arms connected at their proximal ends by a proximal fitting and at their distal ends by a distal fitting, each arm comprising at least one electrode, said basket assembly having an expanded arrangement wherein the arms bow radially outwardly and a collapsed arrangement wherein the arms are generally straight and are arranged generally along the axis of the catheter tip section; the length of the basket assembly in its expanded arrangement being from about 20 mm to about 60 mm and the diameter of the basket assembly in its expanded arrangement being from about 10 mm to about 30 mm;

a control handle at the proximal end of the catheter body, said control handle having first and second movable members, each being movable between first and second positions;

a first puller wire comprising a proximal end attached to the first movable member of the handle, and extending through the catheter body and into an off-axis lumen in the tip section, the distal end of the first puller wire being anchored to the tip section so that movement of the first movable member from a first to a second position results in longitudinal movement of the first puller wire relative to the catheter body and deflection of the tip section, a second puller wire comprising a proximal end attached to the second movable member of the handle and extending through a lumen in the catheter body and a lumen of the tip section and the proximal fitting, the distal end of the second puller wire being attached to the distal fitting of the basket assembly such that movement of the second movable member from a first to a second position results in longitudinal movement of the second puller wire relative to the catheter body and expansion of the basket assembly; and a plurality of electrode lead wires extending through the handle and catheter body, each lead wire attached to a corresponding electrode of the basket assembly.

54. The catheter of claim 53 wherein the length of the basket assembly in its expanded arrangement is from about 20 to about 30 mm.

55. The catheter of claim 53 wherein the diameter of the basket assembly in its expanded arrangement is from about 10 to about 30 mm.

56. The catheter of claim 53 wherein each arm of the basket assembly comprises a metal backbone, at least a portion of which forms an electrode.

57. The catheter of claim 56 wherein the metal backbone of each arm comprises an insulating coating covering at least a portion of the metal backbone.

58. The catheter of claim 57 wherein a middle portion of the metal backbone of each arm is exposed and forms an electrode.

59. The catheter of claim 58 wherein each arm comprises an electrode distal to the exposed portion of the metal backbone.

60. The catheter of claim 58 wherein each arm comprises an electrode proximal to the exposed portion of the metal backbone.

61. The catheter of claim 58 wherein each arm comprises electrodes proximal and distal to the exposed portion of the metal backbone.

* * * * *